United States Patent
Kimura et al.

(10) Patent No.: US 6,723,522 B1
(45) Date of Patent: Apr. 20, 2004

(54) SODIUM BICARBONATE COTRANSPORTER PROTEIN

(75) Inventors: Hiroyuki Kimura, Sakai (JP); Tomohiro Kawamoto, Ibaraki (JP); Hidekazu Sawada, Neyagawa (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/868,572

(22) PCT Filed: Dec. 20, 1999

(86) PCT No.: PCT/JP99/07149
§ 371 (c)(1),
(2), (4) Date: Jun. 20, 2001

(87) PCT Pub. No.: WO00/37637
PCT Pub. Date: Jun. 29, 2000

(30) Foreign Application Priority Data

Dec. 21, 1998 (JP) ............................................. 10-362190

(51) Int. Cl.$^7$ ........................ C07N 14/00; C12N 15/63; C12N 15/12; G01N 33/566
(52) U.S. Cl. ..................... 435/7.2; 435/320.1; 435/325; 435/69.1; 530/350
(58) Field of Search .......................... 530/350; 435/7.2, 435/320.1, 325, 69.1

(56) References Cited

FOREIGN PATENT DOCUMENTS

| EP | 0892052 | 7/1998 |
| EP | 897982 | 2/1999 |
| WO | 98/53067 | 11/1998 |
| WO | WO 9853067 | * 11/1998 |

OTHER PUBLICATIONS

Stratagene Catalog 1988, p. 39.*
Voet et al. Biochemistry. 1990. John Wiley & Sons, Inc. pp. 126–1128, 228–234.*
Charles E. Burham et al., Cloning and Functional Expression of a Human Kidney Na$^+$:HCO$^{-3}$ Cotransporter*, Journal of Biological Chemistry, vol. 272, No. 31, pp. 19111–19114, 1997.
Abuladze et al., "Molecular Cloning, Chromosomal Localization, Tissue Distribution, and Functional Expression of the Human Pancreatic Sodium Bicarbonate Cotransporter*", The Journal of Biological Chemistry, vol. 273, No. 28, pp. 17689–17695, (Jul. 10, 1998).

Romero et al., "Cloning and functional expression of rNBC, an electrogenic Na$^+$–HCO$^{-3}$ cotransporter from rat kidney", American Journal of Physiology, American Physiological Society, pp. 425–432, (1998).
Romero et al., "Expression cloning and characterization of a renal electrogenic Na$^+$/HCO$^{-3}$ cotransporter", Nature, vol. 387, pp. 409–413, (May 22, 1997).
Kenichi Ishibashi et al., "Molecular cloning of a new sodium bicarbonate cotransporter cDNA from human retina", Biochemical and Biophysical Research Communications, Jul. 1998, vol. 246, No. 2, pp. 535–538.
Frank Thevenod et al., "Cloning and immunolocalization of a rat pancreatic Na+ bicarbonate cotransporter", Biochemical and Biophysical Research Communications, Oct. 1999, vol. 264, No. 1, pp. 291–298.
Inyeong Choi et al., "Cloning and characterization of a human electrogenic Na +–HCO3– cotransporter isoform (hhNBC)", American Journal of Physiology, Mar. 1999, vol. 276, No. 3, pp. C576–C584.
Alexander Pushkin et al., "Cloning, tissue distribution, genomic organization, and functional characterization of NBC3, a new member of the sodium bicarbonate cotransporter family", The Journal of Biological Chemistry, Jun. 1999, vol. 274, No. 23, pp. 16569–16575.

* cited by examiner

*Primary Examiner*—Yvonne Eyler
*Assistant Examiner*—Joseph F. Murphy
(74) *Attorney, Agent, or Firm*—Wenderoth, Lind & Ponack, L.L.P.

(57) ABSTRACT

The present invention relates to a protein having a Na$^+$—HCO$_3^-$ cotransporter activity and a DNA encoding it.

The present protein and the present DNA can be used as or for [1] obtaining an antibody and antiserum, [2] constructing an expression system for the present protein, [3] development of a system for measuring the activity of a Na$^+$—HCO$_3^-$ cotransporter and screening of a drug candidate compound using the same expression system, [4] performing drug design based on the steric structure of a Na$^+$—HCO$_3^-$ cotransporter protein, [5] a reagent for making a probe or a PCR primer in gene diagnosis, [6] making a transgenic animal, or [7] a composition for gene prevention and/or treatment.

8 Claims, 6 Drawing Sheets

SEQUENCE LISTING

```
<160> NUMBER OF SEQ ID NOS: 8

<210> SEQ ID NO 1
<211> LENGTH: 971
<212> TYPE: PRT
<213> ORGANISM: Human

<400> SEQUENCE: 1

Met Ser Leu Phe Ala Phe Cys Ser Gly Leu His His Phe Ser Phe Ile
1               5                   10                  15

Cys Phe Ile Ser Gly Asp Gly Leu Ser Ala Ser Arg His Ser Leu Arg
                20                  25                  30

Thr Gly Leu Ser Ala Ser Asn Leu Ser Leu Arg Gly Glu Ser Pro Leu
            35                  40                  45

Ser Leu Leu Leu Gly His Leu Leu Pro Ser Ser Arg Ala Gly Thr Pro
        50                  55                  60

Ala Gly Ser Arg Cys Thr Thr Pro Val Pro Thr Pro Gln Asn Ser Pro
65                  70                  75                  80
```

-continued

```
Pro Ser Ser Pro Ser Ile Ser Arg Leu Thr Ser Arg Ser Ser Gln Glu
            85                  90                  95

Ser Gln Arg Gln Ala Pro Glu Leu Leu Val Ser Pro Ala Ser Asp Asp
            100                 105                 110

Ile Pro Thr Val Val Ile His Pro Glu Glu Asp Leu Glu Ala Ala
            115                 120                 125

Leu Lys Gly Glu Glu Gln Lys Asn Glu Glu Asn Val Asp Leu Thr Pro
130                 135                 140

Gly Ile Leu Ala Ser Pro Gln Ser Ala Pro Gly Asn Leu Asp Asn Ser
145                 150                 155                 160

Lys Ser Gly Glu Ile Lys Gly Asn Gly Ser Gly Ser Arg Glu Asn
            165                 170                 175

Ser Thr Val Asp Phe Ser Lys Val Asp Met Asn Phe Met Arg Lys Ile
            180                 185                 190

Pro Thr Gly Ala Glu Ala Ser Asn Val Leu Val Gly Glu Val Asp Phe
            195                 200                 205

Leu Glu Arg Pro Ile Ile Ala Phe Val Arg Leu Ala Pro Ala Val Leu
            210                 215                 220

Leu Thr Gly Leu Thr Glu Val Pro Val Pro Thr Arg Phe Leu Phe Leu
225                 230                 235                 240

Leu Leu Gly Pro Ala Gly Lys Ala Pro Gln Tyr His Glu Ile Gly Arg
            245                 250                 255

Ser Ile Ala Thr Leu Met Thr Asp Glu Ile Phe His Asp Val Ala Tyr
            260                 265                 270

Lys Ala Lys Asp Arg Asn Asp Leu Leu Ser Gly Ile Asp Glu Phe Leu
            275                 280                 285

Asp Gln Val Thr Val Leu Pro Pro Gly Glu Trp Asp Pro Ser Ile Arg
            290                 295                 300

Ile Glu Pro Pro Lys Ser Val Pro Ser Gln Glu Lys Arg Lys Ile Pro
305                 310                 315                 320

Val Phe His Asn Gly Ser Thr Pro Thr Leu Gly Glu Thr Pro Lys Glu
            325                 330                 335

Ala Ala His His Ala Gly Pro Glu Leu Gln Arg Thr Gly Arg Leu Phe
            340                 345                 350

Gly Gly Leu Ile Leu Asp Ile Lys Arg Lys Ala Pro Phe Phe Leu Ser
            355                 360                 365

Asp Phe Lys Asp Ala Leu Ser Leu Gln Cys Leu Ala Ser Ile Leu Phe
            370                 375                 380

Leu Tyr Cys Ala Cys Met Ser Pro Val Ile Thr Phe Gly Gly Leu Leu
385                 390                 395                 400

Gly Glu Ala Thr Glu Gly Arg Ile Ser Ala Ile Glu Ser Leu Phe Gly
            405                 410                 415

Ala Ser Leu Thr Gly Ile Ala Tyr Ser Leu Phe Ala Gly Gln Pro Leu
            420                 425                 430

Thr Ile Leu Gly Ser Thr Gly Pro Val Leu Val Phe Glu Lys Ile Leu
            435                 440                 445

Tyr Lys Phe Cys Arg Asp Tyr Gln Leu Ser Tyr Leu Ser Leu Arg Thr
            450                 455                 460

Ser Ile Gly Leu Trp Thr Ser Phe Leu Cys Ile Val Leu Val Ala Thr
465                 470                 475                 480

Asp Ala Ser Ser Leu Val Cys Tyr Ile Thr Arg Phe Thr Glu Glu Ala
            485                 490                 495

Phe Ala Ala Leu Ile Cys Ile Ile Phe Ile Tyr Glu Ala Leu Glu Lys
```

-continued

```
                500                 505                 510
Leu Phe Asp Leu Gly Glu Thr Tyr Ala Phe Asn Met His Asn Asn Leu
            515                 520                 525

Asp Lys Leu Thr Ser Tyr Ser Cys Val Cys Thr Glu Pro Pro Asn Pro
    530                 535                 540

Ser Asn Glu Thr Leu Ala Gln Trp Lys Lys Asp Asn Ile Thr Ala His
545                 550                 555                 560

Asn Ile Ser Trp Arg Asn Leu Thr Val Ser Glu Cys Lys Lys Leu Arg
                565                 570                 575

Gly Val Phe Leu Gly Ser Ala Cys Gly His His Gly Pro Tyr Ile Pro
            580                 585                 590

Asp Val Leu Phe Trp Cys Val Ile Leu Phe Phe Thr Thr Phe Phe Leu
        595                 600                 605

Ser Ser Phe Leu Lys Gln Phe Lys Thr Lys Arg Tyr Phe Pro Thr Lys
    610                 615                 620

Val Arg Ser Thr Ile Ser Asp Phe Ala Val Phe Leu Thr Ile Val Ile
625                 630                 635                 640

Met Val Thr Ile Asp Tyr Leu Val Gly Val Pro Ser Pro Lys Leu His
                645                 650                 655

Val Pro Glu Lys Phe Glu Pro Thr His Pro Glu Arg Gly Trp Ile Ile
            660                 665                 670

Ser Pro Leu Gly Asp Asn Pro Trp Trp Thr Leu Leu Ile Ala Ala Ile
        675                 680                 685

Pro Ala Leu Leu Cys Thr Ile Leu Ile Phe Met Asp Gln Gln Ile Thr
    690                 695                 700

Ala Val Ile Ile Asn Arg Lys Glu His Lys Leu Lys Lys Gly Ala Gly
705                 710                 715                 720

Tyr His Leu Asp Leu Leu Met Val Gly Val Met Leu Gly Val Cys Ser
                725                 730                 735

Val Met Gly Leu Pro Trp Phe Val Ala Ala Thr Val Leu Ser Ile Ser
            740                 745                 750

His Val Asn Ser Leu Lys Val Glu Ser Glu Cys Ser Ala Pro Gly Glu
        755                 760                 765

Gln Pro Lys Phe Leu Gly Ile Arg Glu Gln Arg Val Thr Gly Leu Met
    770                 775                 780

Ile Phe Ile Leu Met Gly Leu Ser Val Phe Met Thr Ser Val Leu Lys
785                 790                 795                 800

Phe Ile Pro Met Pro Val Leu Tyr Gly Val Phe Leu Tyr Met Gly Val
                805                 810                 815

Ser Ser Leu Lys Gly Ile Gln Leu Phe Asp Arg Ile Lys Leu Phe Gly
            820                 825                 830

Met Pro Ala Lys His Gln Pro Asp Leu Ile Tyr Leu Arg Tyr Val Pro
        835                 840                 845

Leu Trp Lys Val His Ile Phe Thr Val Ile Gln Leu Thr Cys Leu Val
    850                 855                 860

Leu Leu Trp Val Ile Lys Val Ser Ala Ala Val Val Phe Pro Met Met
865                 870                 875                 880

Met Val Leu Ala Leu Val Phe Val Arg Lys Leu Met Asp Leu Cys Phe
                885                 890                 895

Thr Lys Arg Glu Leu Ser Trp Leu Asp Asp Leu Met Pro Glu Ser Lys
            900                 905                 910

Lys Lys Lys Glu Asp Asp Lys Lys Lys Glu Lys Glu Glu Ala Glu
        915                 920                 925
```

```
Arg Met Leu Gln Asp Asp Asp Thr Val His Leu Pro Phe Glu Gly
         930                 935                 940
Gly Ser Leu Leu Gln Ile Pro Val Lys Ala Leu Lys Tyr Ser Asn Ile
945                 950                 955                 960
Phe Ser Ala Lys Val Ile Arg Gly His His Cys
                965                 970

<210> SEQ ID NO 2
<211> LENGTH: 3157
<212> TYPE: DNA
<213> ORGANISM: Human

<400> SEQUENCE: 2 cttttttaaaa atgccatgct attggtcatt ctaatttcta acaggatatt gcccccacca      60
tctgtcatta acaatttttt tttatgtgtt ctgagaacta attacagttt taaccaactt     120
tttagtgact ttctaacatg taaaaacccg attgacatgc taaccatcac atgactttga     180
aattttgggc ctttgaagta tgcaatttat agtgtaaatt gattttttt taaatgtctc      240
tatttgcctt ctgcagtgga cttcatcatt tttcatttat ttgttttatc tcaggggatg     300
gcctttcagc ctcccgccac tctttgcgaa caggtctgtc tgcctcaaac ctttccttga     360
gaggagaatc acctttatct cttcttctcg gtcatcttct tccttcttca agagctggaa     420
cccctgcagg ctcaaggtgt acaaccccag tacccacccc tcaaaacagt cctccttcta     480
gccctagcat cagccgcctg acctccagaa gttcccaaga gagtcagcgt caggccccag     540
aactactggt ttcacctgcc agtgatgata ttcccacagt agtaattcat ccgcctgagg     600
aagacttaga agcagcgctg aaaggcgagg agcagaagaa tgaggaaaat gttgacttaa     660
ctccaggtat tttggcctct ccccagtctg ctcctggaaa cttggacaat agtaaaagtg     720
gagaaattaa aggtaatgga agtggtggaa gcagagaaaa tagtactgtt gacttcagca     780
aggttgatat gaatttcatg agaaaaattc ctacgggtgc tgaggcatcc aacgtcctgg     840
tgggcgaagt agacttttttg gaaaggccaa taattgcatt tgtgagactg ctcctgctg     900
tcctccttac agggttgact gaggtccctg ttccaaccag gttttttgttt tgttattgg    960
gtccagcggg caaggcacca cagtaccatg aaattggacg atcaatagcc actctcatga    1020
cagatgagat tttccatgat gtagcttata aagcaaaaga cagaaatgac ctcttatctg    1080
gaattgatga attttagat caagtaactg tcctacctcc aggagagtgg gatccttcta    1140
tacgcataga accaccaaaa agtgtccctt ctcaggaaaa gagaaagatt cctgtgtttc    1200
acaatggatc tacccccaca ctgggtgaga ctccctaaaga ggccgctcat catgctgggc    1260
ctgagctaca gaggactgga cggcttttttg gtggtttgat acttgacatc aaaaggaaag    1320
cacctttttt cttgagtgac ttcaaggatg cattaagcct gcagtgcctg gcctcgattc    1380
ttttcctata ctgtgcctgt atgtctcctg taatcacttt tggagggctg cttggagaag    1440
ctacagaagg cagaataagt gcaatagagt ctcttttttgg agcatcatta actgggattg    1500
cctattcatt gtttgctggg caacctctaa caatattggg gagcacaggt ccagttctag    1560
tgtttgaaaa aatttttatat aaattctgca gagattatca actttcttat ctgtctttaa    1620
gaaccagtat tggtctgtgg acttcttttt tgtgcattgt tttggttgca acagatgcaa    1680
gcagccttgt gtgttatatt actcgattta cagaagaggc ttttcagcc cttattttgca    1740
tcatattcat ctacgaggct ttggagaagc tctttgattt aggagaaaca tatgcattta    1800
atatgcacaa caacttagat aaactgacca gctactcatg tgtatgtact gaacctccaa    1860
```

```
accccagcaa tgaaactcta gcacaatgga agaaagataa tataacagca cacaatattt    1920
cctggagaaa tcttactgtt tctgaatgta aaaaacttcg tggtgtattc ttggggtcag    1980
cttgtggtca tcatggacct tatattccag atgtgctctt tggtgtgtc atcttgtttt     2040
```


```
accccagcaa tgaaactcta gcacaatgga agaaagataa tataacagca cacaatattt    1920
cctggagaaa tcttactgtt tctgaatgta aaaaacttcg tggtgtattc ttggggtcag    1980
cttgtggtca tcatggacct tatattccag atgtgctctt tggtgtgtc  atcttgtttt    2040 tcacaacatt ttttctgtct tcattcctca agcaatttaa gaccaagcgt tactttccta    2100
ccaaggtgcg atcgacaatc agtgattttg ctgtatttct cacaatagta ataatggtta    2160
caattgacta ccttgtagga gttccatctc ctaaacttca tgttcctgaa aaatttgagc    2220
ctactcatcc agagagaggg tggatcataa gcccactggg agataatcct tggtggacct    2280
tattaatagc tgctattcct gctttgcttt gtaccattct catctttatg gatcaacaaa    2340
tcacagctgt aattataaac agaaaggaac acaaattgaa gaaaggagct ggctatcacc    2400
ttgatttgct catggttggc gttatgttgg gagtttgctc tgtcatggga cttccatggt    2460
ttgtggctgc aacagtgttg tcaataagtc atgtcaacag cttaaaagtt gaatctgaat    2520
gttctgctcc aggggaacaa cccaagtttt tgggaattcg tgaacagcgg gttacagggc    2580
taatgatttt tattctaatg ggcctctctg tgttcatgac ttcagtccta agtttattc      2640 caatgcctgt tctgtatggt gttttccttt atatgggagt ttcctcatta aaaggaatcc    2700
agttatttga ccgtataaaa ttatttggaa tgcctgctaa gcatcagcct gatttgatat    2760
acctccgtta tgtgccgctc tggaaggtcc atattttcac agtcattcag cttacttgtt    2820 tggtccttt  atgggtgata aaagtttcag ctgctgcagt ggttttttccc atgatggttc    2880 ttgcattagt gtttgtgcgc aaactcatgg acctgtgttt cacgaagaga gaacttagtt    2940
ggcttgatga tcttatgcca gaaagtaaga aaagaaaga agatgacaaa agaaaaaag    3000 agaaagagga agctgaacgg atgcttcaag acgatgatga tactgtgcac cttccatttg   3060 aaggggaag tctcttgcaa attccagtca aggccctaaa atatagtaac atattttcag    3120
ccaaggtgat cagagggcat cattgctaga gtgctgc                             3157

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 3
aagacagaaa tgacctctta tct                                              23

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
caaaaagccg tccagtcctc tgta                                             24

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5
```

-continued

```
ttgggaattc gtgaacagcg ggttacaggg                                      30

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 6
tagtaagctt gcagcactct agcaatgatg ccctc                                35

<210> SEQ ID NO 7
<211> LENGTH: 665
<212> TYPE: DNA
<213> ORGANISM: Human

<400> SEQUENCE: 7 cttttaaaa atgccatgct attggtcatt ctaatttcta acaggatatt gcccccacca      60
tctgtcatta acaattttt tttatgtgtt ctgagaacta attacagttt taaccaactt    120
tttagtgact ttctaacatg taaaaacccg attgacatgc taaccatcac atgactttga    180
aattttgggc ctttgaagta tgcaatttat agtgtaaatt gatttttttt taaatgtctc    240
tatttgcctt ctgcagtgga cttcatcatt tttcatttat ttgttttatc tcaggggatg    300
gcctttcagc ctcccgccac tctttgcgaa caggtctgtc tgcctcaaac ctttccttga    360
gaggagaatc accttatct cttcttctcg gtcatcttct tccttcttca agagctggaa     420
cccctgcagg ctcaaggtgt acaaccccag tacccacccc tcaaaacagt cctccttcta    480
gccctagcat cagccgcctg acctccagaa gttcccaaga gagtcagcgt caggccccag    540
aactactggt ttcacctgcc agtgatgata ttcccacagt agtaattcat ccgcctgagg    600
aagacttaga agcagcgctg aaaggcgagg agcagaagaa tgaggaaaat gttgacttaa    660
ctcca                                                                665

<210> SEQ ID NO 8
<211> LENGTH: 507
<212> TYPE: DNA
<213> ORGANISM: Human

<400> SEQUENCE: 8
ccttggagac tagaaagaaa ctgctagatg gctgtaacac agttcatcca tttccgtgaa     60
gagatcatgg ggaatatgtt cttcatcatc atcttcagta ccaaggataa actgtgttac    120
agagatggag aagaatatga atggaaagaa actgctagat ggctgaaatt tgaagaggat    180
gttgaagatg gcggtgaccg atggagtaaa ccttatgtgg caactctctc tttgcacagt    240
ctttttgaac taaggagttg catcctcaat ggaacagtca tgctggatat gagagcaagc    300
actctagatg aaatagcaga tatggtatta gacaacatga tagcttctgg ccaattagac    360
gagtccatac gagagaatgt cagagaagct cttctgaaga gacatcatca tcagaatgag    420
aaaagattca ccagtcggat tcctcttgtt cgatcttttg cagatatagg caagaaacat    480
tctgaccctc acttgcttga aaggaat                                        507
```

SODIUM BICARBONATE COTRANSPORTER PROTEIN

BACKGROUND OF THE INVENTION

1. Field of the Invention

The present invention relates to a protein having an amino acid sequence identical to or substantially identical to an amino acid sequence represented by SEQ ID NO.: 1 (preferably, a protein having the $Na^+$—$HCO_3^-$ cotransporter activity: hereinafter, abbreviated as present protein in some cases) or a salt thereof and a DNA encoding it.

2. Description of the Related Art

The organisms maintain and regulate the intracellular ionic environment so that the cellular functions such as proliferation, differentiation, contraction and secretion can exert to a maximum extent as necessary. In order to regulate the ionic environment to the conditions optimal for existence, there are a plurality of transporter proteins transporting ions such as $Na^+$, $Ca^{2+}$, $H^+$ and $HCO_3^-$ in a plasma membrane. A $Na^+$—$HCO_3^-$ cotransporter belonging to such the transporter is driven by the concentration gradient of $Na^+$ inside and outside a cellular membrane, and take one $Na^+$ into a cell together with one or more $HCO_3^-$ ions [Cellular Molecular Biology, 3rd edition, translated under supervision by Keiko Nakamura et al., Kyoikusha]. Since the structure of a protein such as an enzyme which functions in cells is greatly affected by pH, there is an optimal pH for the protein function. For that reason, maintenance and regulation of an intracellular pH is extremely important to cells for maintaining homeostasis of the cellular function. Since a $Na^+$—$HCO_3^-$ cotransporter exists in the cell membrane and $HCO_3^-$ taken into cells by a $Na^+$—$HCO_3^-$ cotransporter neutralizes $H^+$ in a cytoplasmic sol, it plays an important role in regulating an intracellular pH like a $Na^+$—$H^+$ exchanger [Cellular Molecular Biology, 3rd edition, translated under supervision by Keiko Nakamura et al., Kyoikusha].

In addition, the $Na^+$—$HCO_3^-$ cotransporter is present in a proximal convoluted uriniferous tubule of a kidney and exerts in resorting $HCO_3^-$ from a glomerulus filtrate in cooperation with a $Na^+$—$H^+$ exchanger [The Journal of Biological Chemistry, 272, 19111 (1997)].

The $Na^+$—$HCO_3^-$ cotransporter plays an important role in maintaining the cell homeostasis at a normal time, and is involved in occurrence of cell disorder at an ischemic time. Since intracellular acidosis is caused by ischemia and a $Na^+$—$HCO_3$— cotransporter and a $Na^+$—$H^+$ exchanger function in order to regulate the decrease in pH. As a result, the intracellular $Na^+$ concentration is elevated and the overload of $Ca^{2+}$ into cells is caused via a $Na^+$—$Ca^{2+}$ exchanger. Consequently, this overloaded $Ca^{2+}$ is considered to be one of factors causing cell disorder [Basic Research in Cardiology, 91, 191 (1996)].

The kidney-derived $Na^+$—$HCO_3^-$ cotransporter gene has been cloned from an amphibian [Nature, 387, 409(1997)]], a rat [American Journal of Physiology, 274, F425(1998)], and a human being [The Journal of Biological Chemistry, 272, 19111, (1997)]. However, a $Na^+$—$HCO_3^-$ cotransporter gene which is expressed in mainly organs other than kidney such as heart and brain has not hitherto been known.

SUMMARY OF THE INVENTION

The object of the present invention is to provide a protein having an amino acid sequence identical to or substantially identical to an amino acid sequence represented by SEQ ID NO.: 1 (preferably, a protein having the $Na^+$—$HCO_3^-$ cotransporter activity), a partial peptide thereof, or a salt thereof, a DNA encoding a protein having an amino acid sequence identical to or substantially identical to an amino acid sequence represented by the SEQ ID NO.: 1 (preferably, a protein having the $Na^+$—$HCO_3^-$ cotransporter activity), or a partial peptide thereof, a recombinant vector containing the DNA, a transformant harboring the recombinant vector a process for producing a protein having an amino acid sequence identical to or substantially identical to an amino acid sequence represented by the SEQ ID NO.: 1 (preferably, a protein having the $Na^+$—$HCO_3^-$ cotransporter activity), or a salt thereof, an antibody to a protein having an amino acid sequence identical to or substantially identical to an amino acid sequence represented by the SEQ ID NO.: 1 (preferably, a protein having the $Na^+$—$HCO_3^-$ cotransporter activity), a partial peptide thereof, or a salt thereof, a method for screening a compound which alters the $Na^+$—$HCO_3^-$ cotransporter activity of a protein having an amino acid sequence identical to or substantially identical to an amino acid sequence represented by the SEQ ID NO.: 1 (preferably, a protein having the $Na^+$—$HCO_3^-$ cotransporter activity), or a salt thereof, a compound obtained by the screening method, or a salt thereof, and a pharmaceutical composition containing the compound or a salt thereof.

The present inventors studied extensively and, as a result, we isolated a cDNA encoding a $Na^+$—$HCO_3^-$ cotransporter protein specifically expressed in a human-derived heart, analyzed the whole nucleotide sequence and, thereafter, succeeded in expression of it in a cell. And, based on these findings, the present inventors further studied, which resulted in completion of the present invention.

That is, the present invention relates to:

(1) a protein having an amino acid sequence identical to or substantially identical to an amino acid sequence represented by SEQ ID NO.: 1, or a salt thereof, (2) a protein described in (1) above having a $Na^+$—$HCO_3^-$ cotransporter activity, or a salt thereof, (3) a partial peptide of the protein described in (1) above, or an amide thereof, or an ester thereof, or a salt thereof, (4) a DNA containing the DNA having a nucleotide sequence encoding the protein described in (1) above, (5) the DNA described in (4) above having a nucleotide sequence represented by SEQ ID NO.: 2, (6) a recombinant vector containing the DNA described in (5) above, (7) a transformant transformed with the recombinant vector described in (6) above, (8) a method for producing the protein described in (1) above, or a salt thereof, which comprises culturing the transformant described in above (7), to produce the protein described in (1) above which is accumulated and taken, (9) an antibody against the protein described in (1) above, or a salt thereof, or the partial peptide described in (3) above, or an amide thereof, or an ester thereof, or a salt thereof,

(10) a method for screening a compound, or a salt thereof, which promotes or inhibits a $Na^+$—$HCO_3^-$ cotransporter activity of the protein described in (1) above, or a salt thereof, or the partial peptide described in (3) above, or an amide thereof, or an ester thereof, or a salt thereof, which comprises using the protein described in (1) above, or a salt thereof, or the partial peptide described in (3) above, or an amide thereof, or an ester thereof, or a salt thereof,

(11) a kit for screening a compound, or a salt thereof, which promotes or inhibits a Na$^+$—HCO$_3^-$ cotransporter activity of the protein described in (1) above, or a salt thereof, or the partial peptide described in (3) above, or an amide thereof, or an ester thereof, or a salt thereof, which comprises the protein described in (1) above, or a salt thereof, or the partial peptide thereof described in (3) above, or an amide thereof, or an ester thereof, or a salt thereof,

(12) a compound or a salt thereof which promotes or inhibits a Na$^+$—HCO$_3^-$ cotransporter activity of the protein described in (1) above, or a salt thereof, or the partial peptide described in claim 3, or an amide thereof, or an ester thereof, or a salt thereof, which is obtainable by using the screening method described in (10) above or the kit for screening described in (11) above,

(13) a pharmaceutical composition which comprises a compound or a salt thereof which promotes or inhibits a Na$^+$—HCO$_3^-$ cotransporter activity of the protein described in (1) above, or a salt thereof, or the partial peptide described in (3) above, or an amide thereof, or an ester thereof, or a salt thereof, which is obtainable by using the screening method described in (10) above or the kit for screening described in (11) above,

(14) the pharmaceutical composition described in (13) above which is a composition for preventing and/or treating for cardiac infarction or dysfunction accompanying therewith, unstable angina, restenosis after PTCA, arrhythmia, heart failure, hypertension and tissue disorder accompanying therewith, cerebral infarction, cerebral hemorrhage, subarachnoid hemorrhage and cerebral disorder accompanying therewith,

(15) a composition for diagnosing cardiac infarction or dysfunction accompanying therewith, unstable angina, restenosis after PTCA, arrhythmia, heart failure, hypertension and tissue disorder accompanying thereof, cerebral infarction, cerebral hemorrhage, subarachnoid hemorrhage and cerebral disorder accompanying therewith, which comprises the antibody described in (9) above, and

(16) a method for quantitating the protein described in (1) above, or a salt thereof, or the partial peptide described in (3) above, or an amide thereof, or an ester thereof, or a salt thereof, which comprises using the antibody described in (9) above.

More particularly, the present invention provides:

(17) the Na$^+$—HCO$_3^-$ transporter protein described in (1) above or a salt thereof, wherein the protein is a protein containing [1] an amino acid sequence in which 1 or 2 or more (preferably around 1 to 30, more preferably around 1 to 9, further preferably a few (1 or 2)) amino acids in an amino acid sequence represented by SEQ ID NO.: 1 are deleted, [2] an amino acid sequence in which 1 or 2 or more (preferably around 1 to 30, more preferably around 1 to 10, further preferably a few (1) or (2)) amino acids are added to an amino acid sequence represented by SEQ ID NO.: 1, [3] an amino acid sequence in which 1 or 2 or more (preferably around 1 to 30, more preferably around 1 to 10, further preferably a few (1 or 2)) amino acids in an amino acid sequence represented by SEQ ID NO.: 1 are substituted with other amino acids, or [4] an amino acid sequence comprising a combination of them,

(18) the method described in (10) above, wherein the case where the protein described in (1) above, or a salt thereof, or the partial peptide described in (3) above, or an amide thereof, or an ester thereof, or a salt thereof is contacted with a test compound and the contrary case are compared,

(19) a method for screening a compound or a salt thereof which alters a Na$^+$—HCO$_3^-$ cotransporter activity, which comprises comparing the case where a test compound is contacted with a cell containing the protein described in (1) above and the contrary case

(20) a method for screening a compound or a salt thereof which alters a Na$^+$—HCO$_3^-$ cotransporter activity, which comprises comparing the case where a test compound is contacted with the protein described in (1) above which is expressed on a cell membrane of the transformant described in (7) above by culturing the transformant and the contrary case

(21) a compound which alters a Na$^+$—HCO$_3^-$ cotransporter activity of the protein described in (1) above, or a salt thereof, which is obtainable by the screening method described in (18) to (20) above, and

(22) a composition for preventing and/or treating cardiac infarction or dysfunction accompanying therewith, unstable angina, restenosis after PTCA, arrhythmia, heart failure, hypertension and tissue disorder accompanying thereof, cerebral infarction, cerebral hemorrhage, subarachnoid hemorrhage and cerebral disorder accompanying therewith, which comprises a compound or a salt thereof which alters the function of the protein described in (1) above, which is obtainable by the screening method described in (18) to (20) above.

BRIEF DESCRIPTION OF THE DRAWINGS

FIG. 1 shows a nucleotide sequence (nucleotides 234–3149 of SEQ ID No: 2) of a DNA encoding the present heart-derived protein obtained in Example 1, and an amino acid sequence (SEQ ID No: 1) presumed therefrom (continued to FIG. 2).

FIG. 2 shows a nucleotide sequence of a DNA encoding the present heart-derived protein obtained in Example 1, and an amino acid sequence presumed therefrom (continued from FIG. 1 and continued to FIG. 3).

FIG. 3 shows a nucleotide sequence of a DNA encoding the present heart-derived protein obtained in Example 1, and an amino acid sequence presumed therefrom (continued from FIG. 2).

Heart shows heart, Brain shows brain, Placenta shows placenta, Lung shows lung, Liver shows liver, Skeletal Muscle shows skeletal muscle, and Kidney shows kidney. A left numeral (kb) shows a size of a RNA molecular weight marker. A shows an expressed amount of the present human heart-derived protein hNBC2b, and B shows an expressed amount of human retina-derived Na$^+$—HCO$_3^-$ cotransporter protein hNBC2.

Figure 6:
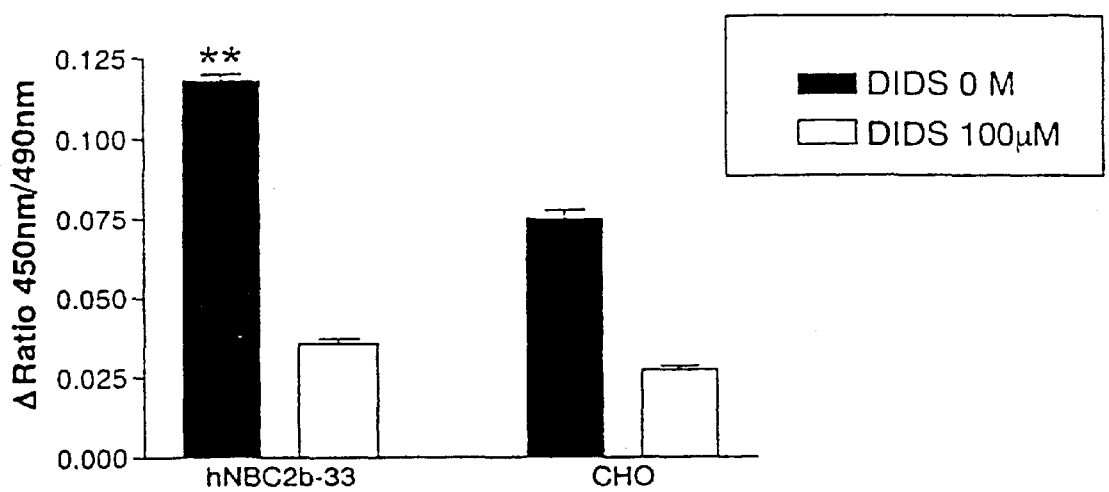

FIG. 6 shows the results obtained by pre-pulsing the hNBC2b-33/CHO-K1 cell which expressed the present human heart-derived protein, with ammonium ion, and, adding a buffer containing sodium ions and bicarbonate ions, and measuring an increased amount of an intracellular pH.

NBC2b-33 shows the hNBC2b-33/CHO-K1 cell which expressed the present heart-derived protein, and CHO-K1 shows the wild-type CHO-K1 cell. A left numeral shows an increased amount of an intracellular pH which was increased during 10 minutes after addition of a buffer containing sodium ions and bicarbonate ions (a ratio value of fluorescent values at 450 nm/490 nm), at a time point of addition of each concentration (final concentration 0, 100 $\mu$M) of DIDS which is an inhibitor for an anionic transporter. Data is expressed as mean±standard error. Comparison between 2 groups was carried out by T test and p<0.001 was determined to be significant.

DESCRIPTION OF THE PREFERRED EMBODIMENTS

Figure 1:
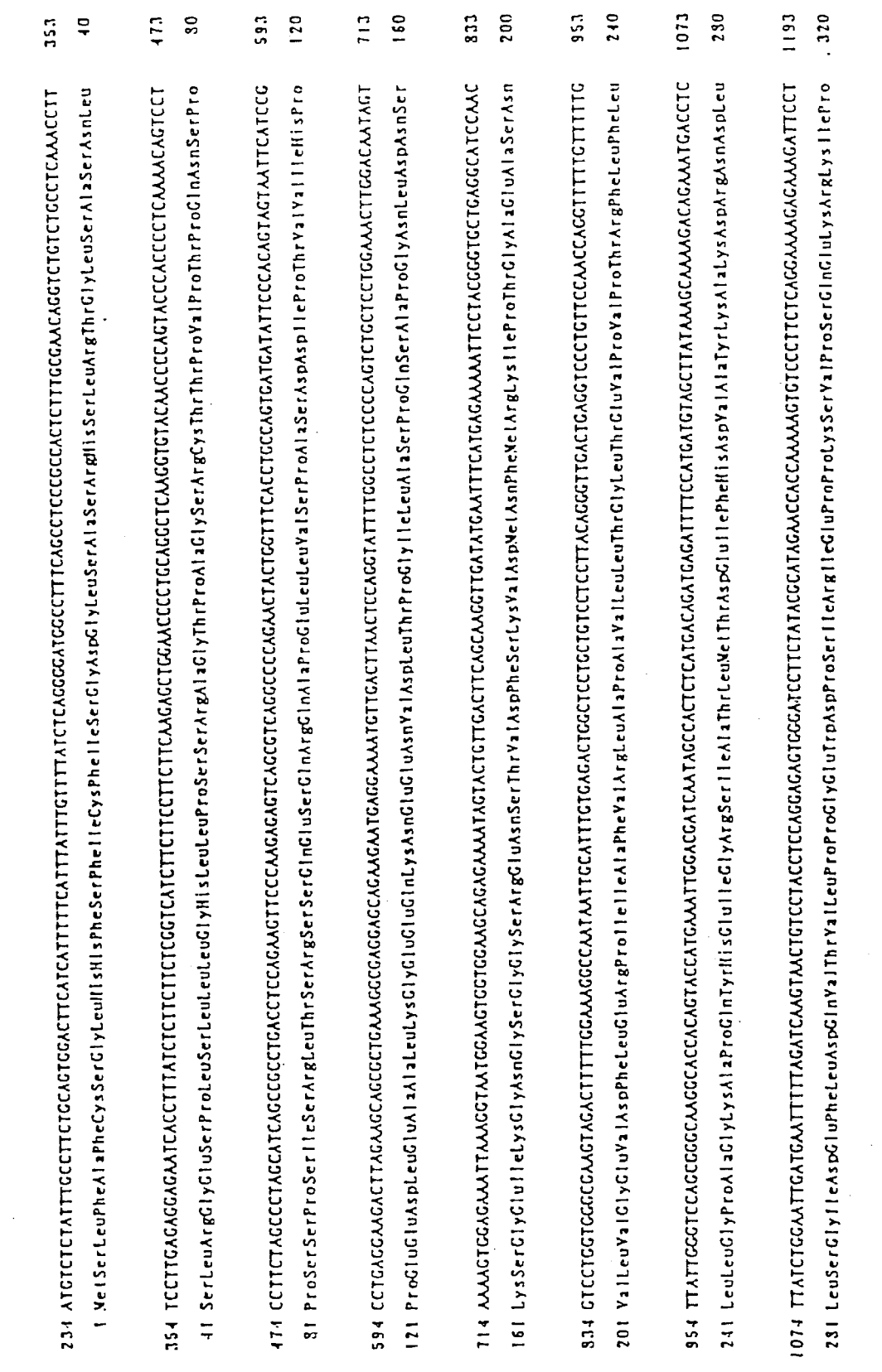
Figure 2:
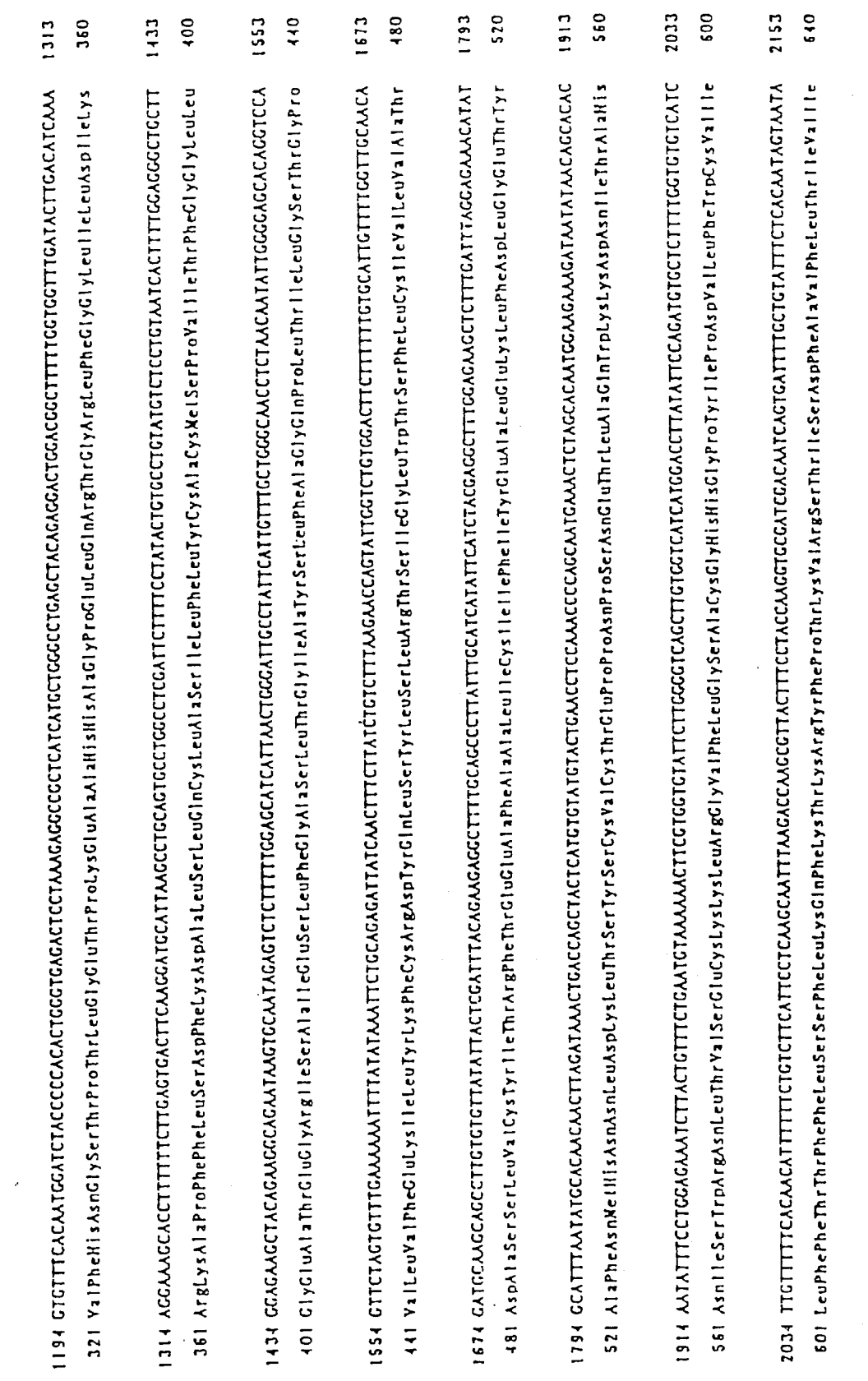
Figure 3:
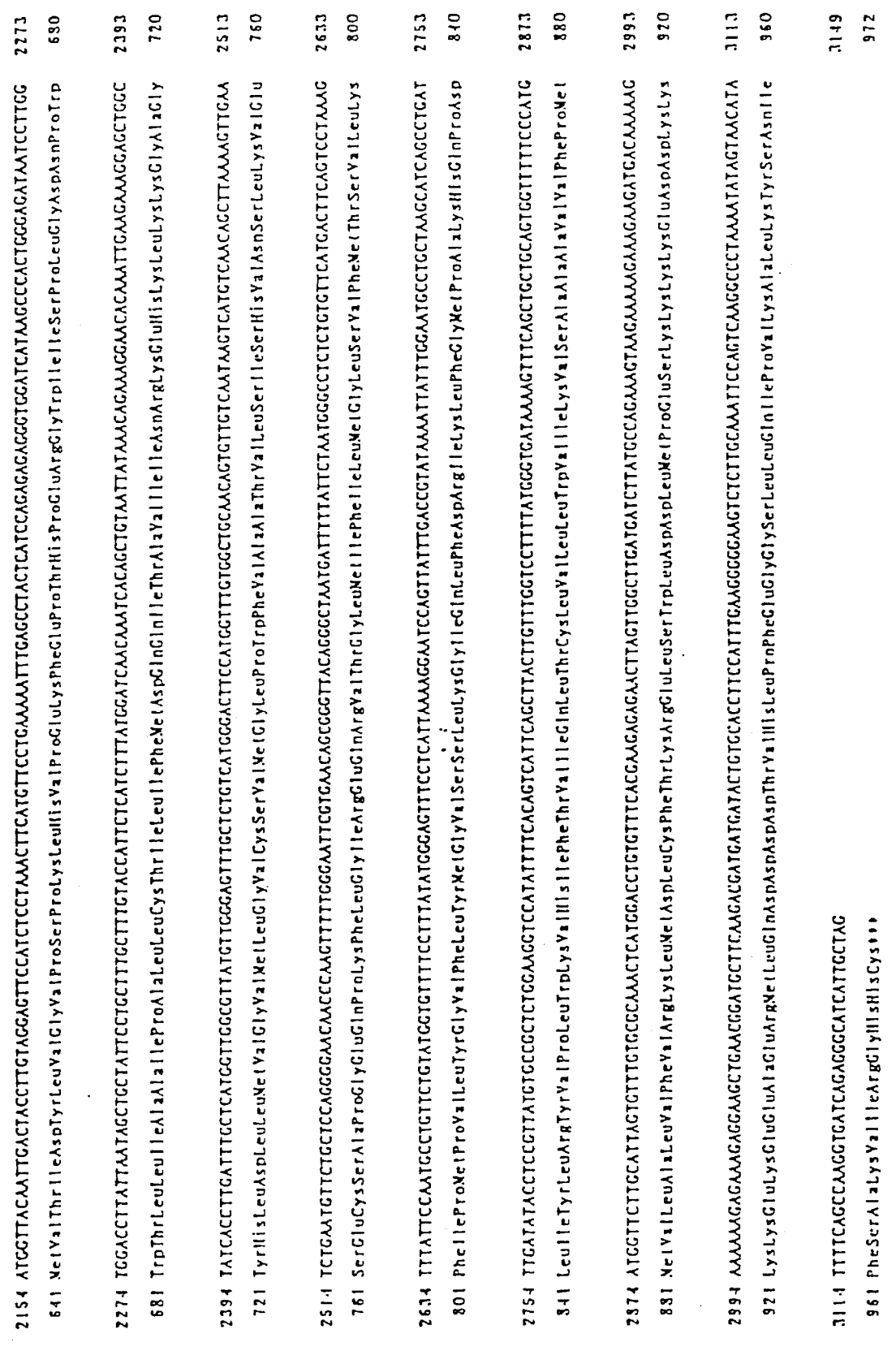

The present protein is a protein containing an amino acid sequence identical to or substantially identical to an amino acid sequence represented by SEQ ID NO.: 1 [FIGS. 1 to 3).

The present protein may be a protein derived, for example, from any cells (for example, spleen cell, nerve cell, glia cell, pancreatic $\beta$ cell, marrow cell, mesangial cell, Langerhans' cell, epidermal cell, epithelial cell, endothelial cell, fibroblast cell, fibrocyte, myocyte, fat cell, immune cell (for example, macrophage, T cell, B cell, natural killer cell, mast cell, neutrophile, basophile, eosinophile, monocyte), megakaryocyte, synovial cell, chondrocyte, bone cell, osteoblast, osteoclast, mammary cell, hepatocyte or interstitial cell, or precursor of these cells, stem cell or cancer cell), or any tissues in which those cells are present such as brain, each part of brain (for example, olfactory bulb, tonsil nucleus, cerebral basal bulb, hippocampus, thalamus, hypothalamus, subthalamic nucleus, cerebral cortex, medulla oblongata, cerebellum, occipital lobe, frontal lobe, temporal lobe, putamen, caudatum, corpus callosum, nigra), spinal cord, pituitary gland, stomach, pancreas, kidney, liver, gonad, thyroid gland, gallbladder, marrow, adrenal gland, skin, muscle, lung, digestive tract (for example, large intestine, small intestine), blood vessel, heart, thymus, spleen, submandibular gonad, peripheral blood, peripheral hemocyte, prostate, testis, testicle, ovary, placenta, uterus, bone, joint, skeletal muscle (in particular, brain and each part of brain) of a human being and a warm-blooded animal (for example, guinea pig, rat, mouse, rabbit, pig, sheep, cow and monkey) or a synthetic protein.

An example of an amino acid substantially identical to an amino acid sequence represented by SEQ ID NO.: 1 includes an amino acid sequence having about 90% or more, preferably about 95% or more, further preferably about 98% or more, most preferably about 99% or more homology with an amino acid sequence represented by SEQ ID NO.: 1.

A preferable example of the present protein containing an amino acid sequence substantially identical to an amino acid sequence represented by SEQ ID NO.: 1 includes a protein having an amino acid sequence substantial identical to an amino acid sequence represented by SEQ ID NO.: 1 and having substantially the same quality of activity as that of an amino acid sequence represented by SEQ ID NO.: 1.

"Substantially the same" means that the activity of a protein, for example, the cotransporter activity ($Na^+$—$CO_3^-$ cotransporter activity etc.) and the physiological properties are substantially the same. Substitution, deletion, addition or insertion of an amino acid does not often greatly alter the physiological properties or chemical properties of polypeptides and, in such a case, a protein with that substitution, deletion, addition or insertion would be substantially the same to a protein without such the substitution, deletion, addition or insertion. Substantially the same substitute for an amino acid in the amino acid sequence can be selected, for example, from other amino acids in a class to which that amino acid belongs.

Examples of a non-polar (hydrophobic) amino acid include alanine, leucine, isoleucine, valine, proline, phenylalanine, tryptophan and methionine. Examples of a polar (neutral) amino acid include glycine, serine, threonine, cysteine, tyrosine, asparagine and glutamine. Examples of a (basic) amino acid having a positive charge include arginine, lysine and histidine. Examples of an (acidic) amino acid having a negative charge include aspartic acid and glutamic acid.

In addition, substantially the same quality indicates that their activities are the same quality in nature (physiochemically or pharmacologically) Therefore, it is preferable that their activities are equal, but quantitative elements such as degrees of these activities and molecular weight may be different.

The cotransporter activity may be measured by the method known per se and, for example, the activity may be measured according to a screening method described below.

In addition, as the present protein, a protein may be used which contains [1] an amino acid sequence in which 1 or 2 or more amino acids in an amino acid sequence represented by SEQ ID NO.: 1 are deleted, [2] an amino acid sequence in which 1 or 2 or more amino acids are added to the amino acid sequence represented by SEQ ID NO.: 1, [3] an amino acid sequence in which 1 or 2 or more amino acids are substituted with other amino acids, in the amino acid sequence represented by SEQ ID NO.: 1 or [4] an amino acid sequence which is a combination thereof. Further, the present protein includes the above-mentioned protein in which an amino group of a methionine residue at a N-terminal is protected with a protecting group (for example, $C_{1-6}$ acyl group such as formyl group and $C_{2-6}$ alkanoyl group such as acetyl), a N-terminal side is cut in the living body to produce Gln which is pyroglutamine-oxidated, a substituent (for example, —OH, —SH, amino group, imidazole group, indole group, guanidino group etc.) on a side chain of an intramolecular amino acid is protected with a suitable protecting group (for example, $C_{1-6}$ acyl group such as formyl group and $C_{2-6}$ alkanoyl group such as acetyl), or a sugar chain is binded thereto (conjugated protein such as so-called glycoprotein).

A partial peptide of the present protein (hereinafter, abbreviated as partial peptide in some cases) may be any partial peptides as long as they are a partial peptide of the aforementioned present protein. For example, a part which is exposed outside a cell membrane among the present protein is used.

Figure 4:
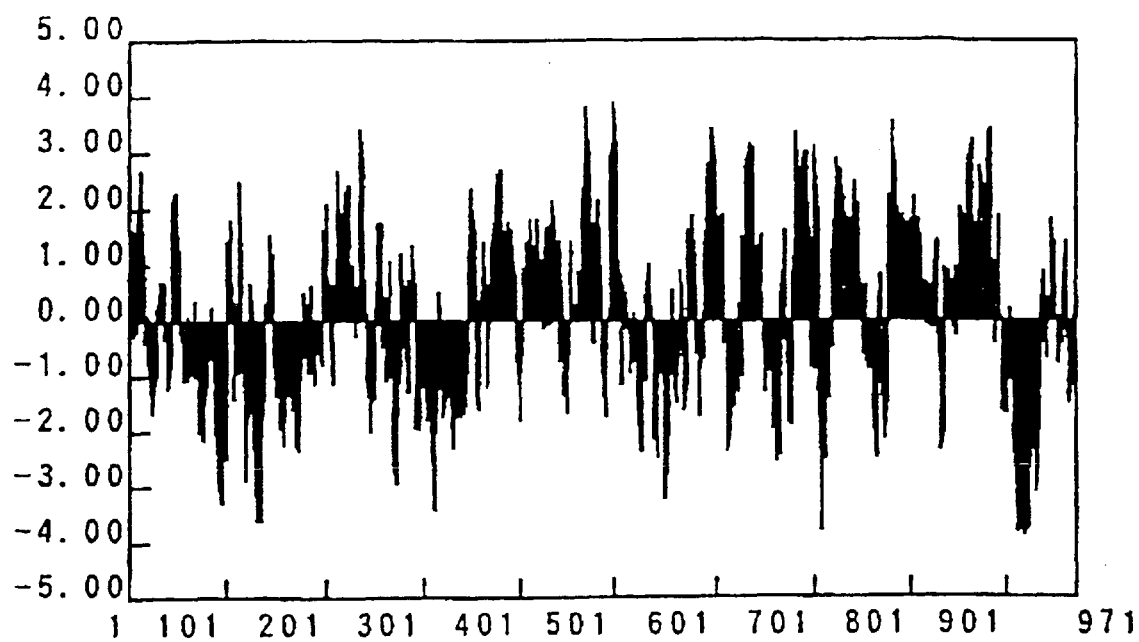
FIG. 4 shows a hydrophobic plot of the present heart-derived protein, which was made based on the amino acid sequence shown in FIGS. 1 to 3. Parts marked with 1 to 10 show a hydrophobic domain.

More specifically, a partial peptide of a protein having an amino acid sequence represented by SEQ ID NO.: 1 is a peptide containing a part which was analyzed to be an extracellular region (Hydrophilic part) in a hydrophobic plotting analysis shown by FIG. 4. In addition, a peptide containing a hydrophobic part as a part may be used similarly. A peptide containing individual domains separately may be used although a peptide of a part containing a plurality of domains simultaneously may be used.

In addition, the present partial peptide may be a partial peptide in which 1 or 2 or more amino acids in the aforementioned amino acid sequence are deleted, or 1 or 2 or more amino acids are added to the amino acid sequence, or 1 or 2 or more amino acids in the amino acid sequence are substituted with other amino acids.

In addition, although a C-terminal of the present protein or partial peptide is usually carboxyl group (—COOH) or carboxylate (—COO$^-$), a C-terminal may be amido (—CONH$_2$) or ester (—COOR) as in the aforementioned present protein.

Examples of R of the ester include $C_{1-6}$ alkyl group such as methyl, ethyl, N-propyl, isopropyl and n-butyl, $C_{3-8}$ cycloalkyl group such as cyclopentyl and cyclohexyl, $C_{6-12}$ aryl group such as phenyl and α-naphthyl, phenyl-$C_{1-2}$ alkyl such as benzyl, phenethyl and benzhydryl, and $C_{7-14}$ aralkyl group such as α-naphthyl-$C_{1-2}$ alkyl such as α-naphthylmethyl, as well as pivaloyloxy methyl group which is widely used as an oral ester.

Further, the present partial peptide includes a partial peptide in which a substituent on a side chain of an intramolecular amino acid is protected with a suitable protecting group, or a conjugated peptide such as so-called glycopeptide in which a sugar chain is binded thereto.

Since the present partial peptide may be used as an antigen for making an antibody, it is not required that it necessarily has the Na$^+$—HCO$_3^-$ cotransporter activity.

As a salt of the present protein or the partial peptide thereof, inter alia, physiologically acceptable acid addition salts are preferable. As such the salt, for example, salts with inorganic acids (for example, hydrochloric acid, phosphoric acid, hydrobromic acid, and sulfuric acid), or salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid) are used.

The present protein, or a salt thereof, or a partial peptide of the present protein, or an amide thereof, or an ester thereof, or a salt thereof may be prepared from the above-mentioned cells or tissues of a human being or a mammal by the purifying method known per se, by culturing a transformant containing a DNA encoding the present protein described below. Alternatively, it may be prepared by a method for synthesizing a protein described below or by the similar method.

When prepared from tissues or cells of a human being or a mammal, tissues or cells of a human being or a mammal are homogenized which is extracted with an acid, and the extract can be purified and isolated by a combination of chromatographies such as reversed phase chromatography and ion exchange chromatography.

A partial peptide of the present protein, or a salt thereof, can be prepared by the method for synthesizing a peptide known per se, or cutting the present protein with a suitable peptidase. A method for synthesizing a peptide may be either of a solid phase synthesizing method or a solution synthesizing method. That is, an end peptide can be prepared by condensing a partial peptide or amino acids which can constitute the present protein with the remaining part and, a product has a protected group, eliminating the protected group. Examples of the known condensing method and elimination of a protecting group are methods described in the following [1] to [5].

[1] M. Bodanszky and M. A. Ondetti, Peptide Synthesis, Interscience Publishers, New York (1966),

[2] Schroeder and Luebke, The Peptide, Academic Press, New York (1965),

[3] Nobuo Izumiya et al, Fundamental and Experiment on Peptide Synthesis, Maruzen K. K. (1975)

[4] Haruaki Yajima and Shunpei Sakakibara, Biochemistry Experimental Course 1, Protein Chemistry IV, 205 (1977),

[5] Development of Medicines, Second Series, vol. 14, Peptide Synthesis, supervised by Haruaki Yajima, Hirokawa Shoten After the reaction, the present partial peptide can be purified and isolated by a combination of the conventional purifying methods, for example, extraction with a solvent, distillation, column chromatography, liquid chromatography and recrystallization. When the partial peptide obtained by the above-mentioned method is a free peptide, it can be converted into a suitable salt according to the known method or the similar method, or conversely when the partial peptide is obtained as a salt, it can be converted into a free peptide or other salt by the known method or the similar method.

An example of a DNA encoding the present protein may be any DNAs as long as they contain a nucleotide sequence encoding the above-mentioned present protein. In addition, the DNA may be a genomic DNA, a genomic DNA library, a cDNA derived from the above-mentioned cells or tissues, a cDNA library derived from the above-mentioned cells or tissues, or a synthetic DNA. A vector used for a library may be any of bacteriophage, plasmid, cosmid and phagemide. Alternatively, a total RNA or a mRNA fraction may be prepared from the above-mentioned cells or tissues, which may be used to amplify a DNA by Reverse Transcriptase Polymerase Chain Reaction (hereinafter, abbreviated as RT-PCR method).

More specifically, examples of a DNA encoding the present protein include a DNA containing a nucleotide sequence represented by SEQ ID NO.: 2, and a DNA encoding a protein having a nucleotide sequence which hybridizes with a nucleotide sequence represented by SEQ ID NO.: 2 under the high stringent conditions and having substantially the same quality of activity (for example, Na$^+$—HCO$_3^-$ cotransporter activity) as that of the present protein.

As a DNA which can hybridize with a nucleotide sequence represented by SEQ ID NO.: 2, a DNA is used which contains a nucleotide sequence having about 90% or more, preferably about 95% or more, more preferably 98% or more, most preferably 99% or more homology with a nucleotide sequence represented by SEQ ID NO.: 2.

Hybridization can be performed by the method known per se or the similar method, for example, a method described in (Molecular Cloning) 2nd (J. Sambrook et al., Colod Spring Harbor Lab. Press, 1989). In addition, when a commercially available library is used, hybridization can be performed by a method described in the attached specification. More preferably, hybridization can be performed according to the high stringent conditions.

The high stringent conditions indicate the conditions of the sodium concentration of about 19 to 40 mM, preferably about 19 to 20 mM, and a temperature of about 50 to 70° C., preferably about 60 to 65° C. In particular, the case of the sodium concentration of about 19 mM and a temperature of about 65° C. is the most preferable.

More particularly, as a DNA encoding a protein containing the amino acid sequence represented by SEQ ID NO.: 1, a DNA may be used which has a nucleotide sequence represented by SEQ ID NO.: 2.

Examples of a DNA encoding the present partial peptide may be any DNAs so long as they contain a nucleotide sequence encoding the above-mentioned present partial peptide. In addition, the DNA may be a genomic DNA, a genomic DNA library, a cDNA derived from the aforementioned cells or tissues, a cDNA library derived from the above-mentioned cells or tissues, or a synthetic DNA. A vector used for a library may be any of bacteriophage, plasmid, cosmid and phagemid. Alternatively, a mRNA fraction is prepared from the above-mentioned cells or tissues, which may be used to amplify a DNA directly by Reverse Transcriptase Polymerase Chain Reaction (hereinafter, abbreviated as RT-PCR method).

More particularly, as a DNA encoding the present partial peptide, for example, [1] a DNA having a partial nucleotide sequence of a DNA having a nucleotide sequence represented by SEQ ID NO.: 2, or [2] a DNA having a nucleotide sequence which hybridizes with a nucleotide sequence represented by SEQ ID NO.: 2 under the high stringent conditions and having a partial nucleotide sequence of a DNA encoding a protein having substantially the same quality of activity (for example, $Na^+$—$HCO_3^-$ cotransporter activity) as that of the present protein are used.

As an example of a DNA which can hybridize with a nucleotide sequence represented by SEQ ID NO.: 2, a DNA may be used which contains a nucleotide sequence having about 90% or more, preferably about 95% or more, more preferably 98% or more, most preferably 99% or more homology with a nucleotide sequence represented by SEQ ID NO.: 2. The similar hybridization method and high stringent conditions to those as described above are used.

An example of cloning of a DNA completely encoding the present protein or a partial peptide thereof (hereinafter, abbreviated as present protein in some cases) includes (1) amplification using by a PCR method using a synthetic DNA primer having a partial nucleotide sequence of the present protein and (2) selection of a DNA incorporated into a suitable vector by hybridization with a labeled DNA fragment or a synthetic DNA encoding a part or an entire region of the present protein. Hybridization can be performed by a method, for example, described in (Molecular Cloning) 2nd (J. Sambrook et al., Cold Spring Harbor Lab. Press, 1989). In addition, when a commercially available library is used, hybridization can be performed according to the attached specification.

Conversion (deletion, addition and substitution) of a nucleotide sequence of a DNA can be performed using the known kit such as Mutan™-G (TAKARA SHUZOU CO., LTD.), and Mutan™-K (TAKARA SHUZOU CO., LTD.) by the method known per se such as Gapped duplex method and Kunkel method or the similar method.

The cloned DNA encoding the present protein can be used as it is or optionally by digesting with a restriction enzyme or adding a linker depending upon the purposes. The DNA may have ATG as a translation initiation codon at its 5'-terminal and may have TAA, TGA or TAG as a translation termination codon as a 3'-terminal. These translation initiation codon and translation termination codon may be added using a suitable synthetic DNA adapter.

An expression vector for the present protein can be prepared, for example, by (a) excising a DNA fragment of interest from a DNA encoding the present protein, and (b) ligating the DNA fragment understream of a promoter in the suitable expression vector.

As a vector, *Escherichia coli*-derived plasmids (for example, pBR322, pBR325, pUC12 and pUC13), *Bacillus subtilis*-derived plasmids (for example, pUB110, pTP5 and pC194), yeast-derived plasmids (for example, pSH19 and pSH15), bacteriophage such as λ-phage, animal virus such as retrovirus, vacciavirus and baculovirus, as well as pA1-11, pXT1, pRc/CMV, pRc/RSV and pcDNAI/Neo are used.

Examples of a promoter used in the present invention may be any promoters as long as they are a suitable promoter depending upon a host used for expressing a gene. For example, when an animal cell is used as a host, there are SRα promoter, SV40 promoter, ltr promoter, CMV (cytomegalovirus) promoter, and HSV-TK promoter. Among them, it is preferable that CMV promoter and SRα promoter are used. When a host is a bacterium of Escherichia genus, trp promoter, LAC promoter, recA promoter, λPL promoter, and lpp promoter are preferable. When a host is a bacterium of Bacillus, SPO1 promoter, SPO2 promoter and penP promoter are preferable. When a host is yeast, PHO5 promoter, PGK promoter, GAP promoter and ADH promoter are preferable. When a host is an insect cell, polyhedrin promoter and P10 promoter are preferable.

Expression vectors optionally containing further enhancer, splicing signal, polyA addition signal, selectable marker and SV40 replication origin (hereinafter, abbreviated as SV40ori in some cases) may be used. Examples of the selectable marker include dihydrofolate reductase (hereinafter, abbreviated as dhfr in some cases) gene [methotrexate (MTX) resistant], ampicillin resistant gene (hereinafter, abbreviated as $Amp^r$ in some cases), and neomycin resistant gene (hereinafter, abbreviated as Neo in some cases, G418 resistant).

In addition, if necessary, a signal sequence suitable for a host is added to a N-terminal of the present protein. When a host is a bacterium of Escherichia genus, PhoA signal sequence, and 0 mpA signal sequence can be utilized. When a host is a bacterium of Bacillus genus, α-amylase signal sequence, and subtilisin signal sequence can be utilized. When a host is yeast, MFα signal sequence and SUS2 signal sequence can be utilized. When a host is an animal cell, insulin signal sequence, α-interferon signal sequence, and antibody molecule signal sequence can be utilized.

The vector containing a DNA encoding the present protein constructed in this way can be used to prepare a transformant.

As a host, for example, bacteria of Escherichia genus, bacteria of Bacillus, yeast, insect cells, insects, and animal cells are used.

Examples of bacteria of Escherichia genus to be used include *Escherichia coli* K 12·DH1 [Proc. Natl. Acad. Sci. USA, vol. 60, 160(1968)], JM103 (Nucleic Acids Research, vol. 9, 309 (1981)], JA221 [Journal of Molecular Biology, vol. 120, 517(1978)], HB101 [Journal of Molecular Biology, vol. 41, 459(1969)], and C600 [Genetics, vol. 39, 440 (1954)].

Examples of the bacteria of Bacillus genus to be used include *Bacillus subtilis* MI114 [Gene, vol. 24, 255(1983)], and 207–21 [Journal of Biochemistry) vol. 95, 87(1984)].

Examples of the yeast to be used include Saccharomyces cerevisiae, AH22, AH22R⁻, NA87-11A, DKD-5D, 20B-12, Schizosaccharomyces pombe NCYC1913, NCYC2036, and Pichia pastoris.

An insect cell, when a virus is AcNPV, may for example be an armyworm-derived cell line, i.e., a *Spodoptera frugiperda* cell (Sf cell), a Trichoplusia ni Medium intestine-derived MG1 cell, a Trichoplusia ni egg-derived high Five™ cell, a Mamestrabrassicae-derived cell or an Estigmena acrea-derived cell. When a virus is BmNPV, a silkworm-derived cell line Bombyx mori N (BmN cell) may be employed. Such Sf cell may for example be an Sf9 cell (ATCC CRL1711), an Sf21 cell (all in Vaughn, J. L. et al., In Vivo, 13,213–217, (1977)).

An insect may for example be a larva of a silkworm [Maeda et al., Nature, vol. 315, 592 (1985)].

An animal cell may for example be a simian COS-7 cell, a Vero cell, a Chinese hamster cell CHO (hereinafter, abbreviated as CHO cell), a dhfr gene-deficient Chinese hamster cell CHO (hereinafter abbreviated as CHO (dhfr⁻) cell), a mouse L cell, a mouse AtT-20 cell, a mouse myeloma cell, a rat GH3 cell, a human FL cell, HEK293 cell, a C127 cell, a BALB3T3 cell, and a Sp-2 cell. Inter alia, a CHO cell, a CHO (dhfr⁻) cell, and HEK293 cell are preferable.

In order to transform an Escherichia microorganism, a method described in Proc. Natl. Acad. Sci. USA, vol. 69, 2110 (1072) or in Gene, vol. 17, 107(1982) may for example be employed.

In order to transform a Bacillus microorganism, a method described in Molecular & General Genetics, vol. 168, 111 (1979) may for example be employed.

In order to transform a yeast, a method described in Methods in Enzymology, vol. 194, 182–187 (1991), or Proc. Natl. Acad. Sci. USA, vol 75, 1929 (1978) may for example be employed. In order to transform an insect cell or an insect, a method described in Bio/Technology, vol. 6, 47–55 (1988) may for example be employed.

An example of a method of introducing an expression vector into an animal cell includes a calcium phosphate method [Graham, F. L. and van der Eb, A., J. Virology 52, 456–467 (1973)], and an electroporation method [Nuemann, E. et al. EMBO J., 1,841,845 (1982)].

As described above, a transformant which has been transformed with an expression vector comprising a DNA encoding a peptide of the invention can be obtained.

In one method for expressing a peptide of the invention stably using an animal cell, a cell in which an expression vector introduced into an animal cell described above is integrated into its chromosome is selected by, means of clone selection. Typically, a transformant is selected using a selectable marker described above as an index. Then by repeating the clone selection in the animal cell obtained using such selection marker, a reliable animal cell capable of expressing a peptide of the invention at a high level can be obtained. When a dhfr gene is used as a selectable marker, the MTX concentration level is raised gradually over the period of incubation to select a resistant strain, in which a DNA encoding an inventive peptide is amplified together with a dhfr gene, whereby obtaining an animal cell line enabling a further higher expression.

A transformant described above is incubated under the conditions allowing a DNA encoding a peptide of the invention to be expressed and then the inventive peptide is produced and accumulated, whereby producing the inventive protein or a salt thereof.

For the incubation of transformant when the host cell is an Escherichia or Bacillus microorganism, a suitable culture medium is a liquid medium, which may contain the components required for the growth of the transformant such as a carbon source, a nitrogen source, an inorganic substance and the like. A carbon source may for example be glucose, dextrin, a soluble starch, sucrose and the like and a nitrogen source may for example be an inorganic or organic materials such as an ammonium salt, a nitrate, corn steep liquor, peptone, casein, a meat extract, a soybean flake, a potato extract and the like, and a mineral may for example be calcium chloride, sodium dihydrogen phosphate, magnesium chloride and the like. Those which may also be added are an yeast extract, vitamins, a growth promoting factor and the like. The pH of a medium is preferably about 5 to 8.

As a culture medium for incubating an Escherichia microorganism, a M9 medium containing glucose and casamino acid [Miller, Journal of Experiments in Molecular Genetics, 431–433, Cold Spring Harbor Laboratory, New York 1972] is preferred. The medium may contain an agent for increasing the promoter efficiency such as 3β-indolylacrylic acid.

When the host cell is an Escherichia microorganism, the incubation is performed usually for about 3 to 24 hours at about 15 to 43° C., optionally with aerating and stirring.

When the host cell is a Bacillus microorganism, the incubation is performed usually for about 6 to 24 hours at about 30 to 40° C. optionally with aerating and stirring.

For the incubation of transformant when the host cell is yeast, a suitable culture medium may for example be a Burkholder minimum medium [Bostian, K. L.,et al., Proc. Natl. Acid. Sci. USA, vol.77, 4505(1980)]or a 0.5% casamino acid-supplemented SD medium [Bitter, G. A. et al., Proc. Natl. Acad. Sci. USA, vol.81, 5330(1984)] and the like. The pH of a midium is adjusted preferably at about 5 to 8. The incubation is performed usually for about 24 to 72 hours at about 20 to 35° C., optionally with aerating and stirring.

For the incubation of transformant when the host cell is an insect cell or an insect, a suitable culture medium may for example to be a Grace's Insect Medium (Grace, T. C. C., Nature, 195, 788(1962)) supplemented appropriately, for example, with an inactivated 10% bovine serum. The pH of a medium is adjusted preferably at about 6.2 to 6.4. The incubation is performed usually for about 3 to 5 days at about 27° C., optionally with aerating and stirring.

For the incubation of transformant when the host cell is an animal cell, a suitable culture medium may for example be an about 5 to 20% fetal calf serum-supplemented MEM medium [Science, vol. 122, 501(1952)], a DMEM medium [Virology, vol.8, 396(1959)], an RPMI 1640 medium [The Journal of the American Medical Association, vol. 199, 519(1967)], a 199 medium [Proceeding of the Society for the Biological Medicine, vol. 73, 1(1950)] and the like. The pH is preferably about 6 to 8. The incubation is performed usually for about 15 to 72 hours at about 30° C. to 40° C., optionally with aerating, and stirring.

As described above, a transformant can express the present protein.

In order to isolate a purified protein of the invention from a culture described above, the following procedure may for example be employed.

For extracting the protein of the invention from a cultured bacterial cell or a cell, a cell is collected by the known method after incubation and suspended in a suitable buffer solution, and then destroyed with a lysozyme and/or a freezing-melting cycle, and then subjected to a centrifugation or a filtration, whereby yielding a crude extract of the protein. The buffer solution may contain a protein modifier such as urea and guanidine hydrochloride or a surfactant such as Triton X-100™.

The present protein contained in an extract obtained in this way may be purified by an appropriate combination of separation and isolation methods known per se. Such known separation and isolation methods include a methods utilizing the solubility such as salting out or a solvent sedimentation, a method utilizing the difference in the melocular weight such as a dialysis, an ultrafiltration, a gel filtration and an SDS-polyacrylamide gel electrophoresis, a method for utilizing the difference in the electric charge such as an ion exchange chromatography, a method utilizing the difference in the hydrophobicity such as a reverse phase high performance liquid chromatography, a method utilizing the difference in the isoelectric point such as an isoelectric focusing and the like.

When the protein of this invention obtained in this way is in a free form, it can be converted into a salt by the method known per se or equivalent, and when it is obtained as a salt it can be converted into a free form or another salt by the method known per se or equivalent.

By bringing the present protein produced by a transformant into contact with a suitable protein-modifying enzyme before or after purification, an optional modification can be carried out or a polypeptide can partially be removed. Such protein-modifying enzyme may for example be trypsin, chymotrypsin, arginylendopeptidase, proteinkinase, glycosidase and the like.

The protein of the invention thus obtained can be identified by an enzyme immunoassay using a specific antibody.

An antibody to the present protein or a salt thereof, or a partial peptide of the present protein, or an amide, or an ester thereof, or a salt thereof (hereinafter, referred to as present protein in some cases) may be a polyclonal antibody or a monoclonal antibody as long as it can recognize the present protein.

An antibody to the present protein can be prepared using the present protein as an antigen according to the method for preparing an antibody or an antiserum known per se.

Preparation of Monoclonal Antibody
(a) Preparation of Monoclonal Antibody Producing Cell The present protein can be administered as it is or together with a carrier or a diluent to a site of a mammal which can produce an antibody. In order to enhance the antibody producing ability upon administration, complete Freund's adjuvant or incomplete Freund's adjuvant may be administered. Administration may be performed usually once every 2 to 6 weeks at a total times of around 2 to 10. Examples of a mammal to be used include monkey, rabbit, dog, guinea pig, mouse, rat, sheep and gout. Mouse and rat are preferably used.

Upon preparation of a monoclonal antibody producing cell, an individual for which antibody titer was recognized is selected from a warm-blooded animal immunized with an antigen, for example, mouse, spleen or lymph node is taken 2 to 5 days after final immunization, and an antibody producing cell contained therein can be used with a homogenous or heterogenous animal's myeloma cell to prepare a monoclonal antibody producing hybridoma. Measurement of an antibody titer in an antiserum can be performed, for example, by reacting the labeled present protein described below with an antiserum and, thereafter, measuring the activity of a labeling agent bound to an antibody. The fusion procedure can be performed by the known method, for example, a method of Keller and Milstein [Nature, vol.256, pp.495 (1975)]. As a fusion promoting agent, for example, there are polyethylene glycol (PEG) and Sendaivirus. Preferably, PEG is used.

Examples of the myeloma cell include a myeloma cell of a warm-blooded animal such as NS-1, P3U1, SP2/0 and AP-a. P3U1 is preferably used. A preferable ratio of the number of an antibody producing cell (spleen) and the number of myeloma cell to be used is around 1:1 to 20:1. Cell fusion can be performed effectively by adding PEG (preferably PEG1000 to PEG6000) at the concentration of around 10 to 80% and incubating at about 20–40° C., preferably 30–37° C. for about 1 to 10 minutes.

For screening a monoclonal antibody producing hybridoma, a number of methods can be used. For example, there are a method of adding a hybridoma culturing supernatant to a solid phase (for example, microplate) onto which the present protein antigen is adsorbed directly or together with a carrier, adding an anti-immunoglobulin antibody (when a cell used for cell fusion is mouse, an anti-mouse immunoglobulin antibody is used) labeled with an radioactive substance or an enzyme, or protein A, and detecting a monoclonal antibody bound to a solid phase, and a method of adding a hybridoma culturing supernatant to a solid phase onto which an anti-immunoglobulin antibody or protein A is absorbed, adding the present protein labeled with a radioactive substance or enzyme, detecting a monoclonal antibody bound to solid phase.

Although selection or a monoclonal antibody can be performed by method known per se or the equivalent method, it can be usually performed on a medium or an animal cell to which HAT (hypoxanthine, aminopterin, thymidine) has been added. As a medium for selection and growth, any medium can be used as long as a hybridoma can grow on the medium. For example, RPMI 1640 medium containing 1 to 20%, preferably 10 to 20% bovine fetal serum, GIT medium containing 1 to 10% bovine fatal serum (Wankojunyakogyo (K.K.)) or serum free medium for caluturing hybridoma (SFM-101, Nissuiseiyaku (K.K.)) can be used. A culturing temperature is usually 20 to 40° C., preferably about 37° C. A culturing time is usually 5 days to 3 weeks, preferably 1 week to 2 weeks. Culturing can be performed usually under 5% carbonic acid gas. An antibody titer in a hybridoma culturing supernatant can be measured as in the aforementioned measurement of an antibody titer in an antiserum.
(b) Purification of Monoclonal Antibody Separation and purification of a monoclonal antibody can be performed according to a method for separating and purifying an immunoglobulin [for example, salting out method, alcohol precipitation method, isoelectric point precipitation method, electrophoresis method, adsorbing or describing method using an ion exchanger (for example DEAE), ultracentrifugation method, gel filtration method, and specific purifying method by taking only an antibody with an antigen-bound solid phase or an active adsorbing agent such as protein A or protein G, and dissociating a bond to obtain antibody] as in the conventional separation and purification of a polyclonal antibody.

Preparation of Polyclonal Antibody

The present polyclonal antibody can be prepared by the method known per se or similar method. For example, the polyclonal antibody can be prepared by making an immune antigen (present protein antigen) itself or a complex of it and a carrier protein, immunizing a mammal as in the aforementioned preparation of a monoclonal antibody, taking a material containing an antibody to the present protein from the immunized animal, and separating and purifying an antibody.

Regarding a complex of an immunization antigen and a carrier protein for immunizing a mammal, a kind of carrier protein and a mixing ratio and carrier and hapten may be any ones so long as an antibody can be effectively binded to a hapten immunized by cross-linking with carrier. For example, a method is used in which bovine serum albumin, bovine thyroglobulin, keyhole limpet hemocyanin and the like is coupled to a hapten at a rate by weight of about 0.1 to 20, preferably about 1 to 5 relative to hapten.

In addition, a variety or condensing agents can be used for coupling a hapten and a carrier, and glutaraldehyde and carbodiimide, maleimide active ester, and active ester regent containing a thiol group or a dithiopyridyl group are used.

A condensed product is administered to a warm-blooded at a site which can produce an antibody as it is or together with a carrier or a diluent. In order to enhance the antibody producing ability upon administration, complete Freund's adjuvant and incomplete Freund's adjuvant may be administered. Administration can be performed usually once every about 2 to 6 weeks at a total of 3 to 10 times.

A polyclonal antibody can be taken from blood or ascites, preferably blood of a mammal immunized by the above-mentioned method.

A polyclonal antibody titer in antiserum can be measured as in the aforementioned measurement of an antibody titer in serum. Separation and purification of a polyclonal antibody can be performed according to the similar method for separating and purifying immunoglobulin to the above-mentioned separation and purification of a monoclonal antibody.

A DNA encoding the present protein, or a salt thereof, or a partial peptide of the present protein, or an amide thereof, or an ester thereof, or a salt thereof (hereinafter, referred to as present DNA in some cases) can be used for or as obtaining an antibody and antiserum, constructing an expression system for the present protein, constructing a system for measuring the activity of a $Na^+$—$HCO_3^-$ cotransporter and screening a drug candidate compound using the same expression system, performing drug design based on the steric structure of a $Na^+$—$HCO_3^-$ cotransporter, a reagent for making a probe or a PCR primer in gene diagnostic, producing a transgenic animal or a composition for gene prevention and/or therapy.

In particular, by using the $Na^+$—$HCO_3^-$ cotransporter activity measuring system using an expression system for the present protein, a compound which alters the $Na^+$—$HCO_3^-$ cotransporter activity specific for a human being or a mammal can be screened and the compound can be used as a composition for preventing and/or treating a variety of diseases.

The uses of the present protein, the present DNA, a cell expressing the present protein and an antibody to the present pretein (hereinafter, abbreviated as present antibody in some cases) will be explained below.

(1) A Method for Screening a Compound Which Alters the Activity of Present Protein A compound (for example, peptide, protein, non-peptidic compound, synthetic compound and fermentation product) which alters the $Na^+$—$HCO_3^-$ cotransporter activity of the present protein or a salt thereof can be effectively screened by using the present protein, or by constructing a system for expressing the present protein and using the $Na^+$—$HCO_3^-$ cotransporter activity measuring system using the expression system.

Such the compound includes a compound which potentiates the $Na^+$—$HCO_3^-$ cotransporter activity of the present protein, or a compound which inhibits the $Na^+$—$HCO_3^-$ cotransporter activity or the present protein.

That is, the present invention provides a method for screening a compound which alters the function (specifically, $Na^+$—$HCO_3^-$ cotransporter activity and the like) of the present protein, or a salt thereof, which comprises comparing the case where a test compound is contacted with the present protein and the case where a test compound is not contacted with the present protein.

More specifically, the present invention provides:

a screening method, which comprises comparing the case where a test compound is contacted with the present protein and the case where the test compound is not contacted with the present protein, a method for screening a compound which alters the function (specifically, $Na^+$—$HCO_3^-$ cotransporter activity) of the present protein, or a salt thereof, which comprises comparing the case where a test compound is contacted with a cell containing the present protein and the case where a test compound is not contacted with a cell containing the present protein and a method for screening a compound which alters the function (specifically, $Na^+$—$HCO_3^-$ cotransporter activity and the like) of the present protein, or a salt thereof, which comprises comparing the case where a test compound is contacted with the present protein expressed on a cell membrane of a transformant containing the present DNA by culturing the transformant and the case where a test compound is not contacted with the present protein expressed on a cell membrane of a transformant containing the present DNA by culturing the transformant.

Before the present protein is obtained, for example, when a compound altering the $Na^+$—$HCO_3^-$ cotransporter activity is screened, a test was necessary in which a candidate compound is first obtained using cells or tissues containing a $Na^+$—$HCO_3^-$ cotransporter protein of a rat (primary screening) and, thereafter, whether the candidate compound is actually a compound altering the activity of a human $Na^+$—$HCO_3^-$ cotransporter or not is confirmed (secondary screening). Since when cells or tissues are used as they are, other transporter proteins are mixed therein, it was difficult to actually screen a compound altering the activity of a $Na^+$—$HCO_3^-$ cotransporter protein of interest.

However, for example, by using a cell expressing the present human-derived protein, the necessity for primary screening is eliminated and a compound altering the $Na^+$—$HCO_3^-$ cotransporter activity can be effectively screened.

The present screening method will be explained more specifically below.

First, as the present protein used for the present screening method, any containing the aforementioned present protein may be used. A cell of an organ of a mammal containing the present protein is suitable. However, since particularly a human-derived organ is extremely difficult to obtain, cells which expressed a human-derived protein are suitable for use in screening.

For constructing a cell which expressed the present protein, the aforementioned method is used. But, it is preferable to construct the cell by expressing the present DNA in a mammal cell or an insect cell. An example of a DNA fragment encoding a protein part of interest to be used includes but is not limited to a complementary DNA. For example, a gene fragment or a synthetic DNA may be used. In order that a DNA fragment encoding the present protein is introduced in a host animal cell and it is effectively expressed, it is preferable to incorporate the DNA fragment downstream of polyhedrin promoter of nuclear polyhedrosis virus (NPV) belonging to Baculovirus for which an insect is a host, SV40-derived promoter, a promoter of a retrovirus, metallothionein promoter, human heat shock promoter, cytomegalovirus promoter or SRα promoter. As a cell used in expression, any cells may be used as long as expression of the present protein can be confirmed. Preferably, a cell which has low $Na^+$—$HCO_3^-$ cotransporter activity is used. Investigation of an amount of quality of the expressed $Na^+$—$HCO_3^-$ cotransporter can be performed by the method known per se. For example, investigation can be performed according to a method of measuring an intracellular pH (The Journal of Biological Chemistry, vol. 272, pp.19111–19114 (1997)), a method of measuring the intracellular sodium ion concentration using a sodium ion indicator (Investigative Ophthalmology and Visual Science ,vol. 33, pp.3068–3079

(1992)), a method for measuring the activity of incorporating labeled sodium into a cell (The Journal of Clinical Investigation, vol.79, pp.1276–1280(1987)), or a method for measuring membrane potential (Nature, vol.387, 409–413 (1997)).

More superficially, first, a cell containing the present protein is cultured on a multiwell plate. After exchanged with a fresh medium or a suitable buffer showing no toxicity to a cell, an intracellular pH indicator such as BCECF is loaded thereon. Thereafter, the buffer is exchanged with a buffer containing ammonium chloride and, after incubated for a period of time, the buffer is exchanged with a suitable buffer containing no ammonium chloride. Thereafter, a test compound is added to incubate a period of time, a buffer containing sodium ions and bicarbonate ions is added and an increase in an intracellular pH thereafter can be measured to perform screening.

As a test compound, for example, peptide, protein, non-peptidic compound, synthetic compound, fermentation product, cell extract, plant extract and animal tissue extract are used. These compounds may be a novel compound or known compound.

A compound which inhibits the activity of the present protein is useful as a safe and low toxic drug for ischemic diseases (for example, cardiac infarction and dysfunction accompanying therewith, unstable, angina and the like), restenosis after PTCA, arrhythmia, heart failure, hypertension and tissue disorder accompanying therewith, ischemic cerebral diseases (for example, cerebral infarction ,cerebral hemorrhage, cerebral disorder accompanying with subarachnoid hemorrhage).

On the other hand, a compound which promotes the activity of the present protein is useful as a safe and low toxic drug for metabolic acidosis accompanied with renal diseases.

When the compound obtained by using the present screening method or a salt thereof is used as the aforementioned pharmaceutical composition, it can be carried out according to the conventional means. For example, the compound or the salt can be formulated into tablets, capsules, elixirs, microcapsules, sterile solutions or suspensions.

Since the thus obtained preparations are safe and low toxic, they can be administered for example to a human being or a mammal (for example, rat, rabbit, sheep, pig, cow, cat, dog and monkey).

A dose of the compound or a salt thereof varies depending upon subject disease, administration subject and administration route and, for example, when an inhibitor for the present protein is orally administered for the purpose of treating cardiac infarction, the inhibitor is generally administered at an amount of about 0.1 mg to 100 mg preferably about 1.0 to 50 mg, more preferably about 1.0 to 20 mg per day in an adult (60 kg). When parentally administered, one time dose of the compound varies depending upon administration subject and subject diseases and, for example, when the inhibitor of the present protein is administered to an adult (60 kg) in the form of an injectable for the purpose of treating cardiac infarction, it is advantageous to administer the inhibitor by intravenous injection at an amount of about 0.01 to 30 mg, preferably about 0.1 to 20 mg, more preferably about 0.1 to 10 mg per day. In the case of other animals, a dose calculated per 60 kg may be administered.

(2) Quantitation of the Present Protein

Since the present antibody can specifically recognize the present protein, it can be used for quantitation of the present protein in a specimen solution, in particular, quantitation by a sandwich immunoassay. That is, for example, the present invention provides:

(i) a method for quantitating the present protein in a specimen solution, which comprises competitively reacting the present antibody with a specimen solution and the labeled present protein, and determining a ratio of the labeled present protein bound to the antibody, (ii) a method for quantitating the present protein in a specimen solution, which comprises simultaneously or continuously reacting a specimen solution with the present antibody insolublized on a carrier and the labeled present antibody, and measuring the activity of a labeling agent on an insolublized carrier.

In the above (ii), it is preferable that one of antibodies is an antibody which recognizes a N-terminal of the present protein and the other of the antibodies is an antibody which reacts with a C-terminal of the present protein.

Not only measurement of the present protein can be performed using a monoclonal antibody for the present protein (hereinafter, referred to as the present monoclonal antibody in some cases), but also detection by tissue staining can be performed. For these purposes, an antibody molecule itself may be used, or, alternatively, F (ab')$_2$, Fab' or Fab fraction of an antibody molecule may be used. A method for measurement using the antibody for the present protein is not particularly limited but any measuring methods may be used as long as they are a method for measurement by detecting an amount of an antibody, an antigen or an antibody-antigen complex corresponding to an amount of an antigen in a specimen solution (for example, an amount of the present protein) by chemical or physical means, and calculating this amount from a standard curve made using a standard solution containing the known amount of an antigen. Although, for example, nephrometery, competitive method, immunometric method and sandwich method are suitably used, it is particularly preferable to use a sandwich method described below in respect of the sensitivity and the specificity.

As a labeling agent used for a measuring method using a label in substance, for example, radioisotope elements, enzymes, fluorescent substances and emission substances are used. As the radioisotope element, for example, [$^{125}$I], [$^{131}$I], [$^3$H] and [$^{14}$C] are used. As the above enzyme, an enzyme which is stable and has large specific activity is preferable and, for example, β-galactosidase, β-glucosidase, alkaline phosphatase, peroxidase and malate dehydrogenase are used. As the fluorescent substance, for example, fluorescamine and fluorescein isothiocyanate are used. As the emission substance, for example, luminol, luminol derivative, luciferin and lucigenin are used. Further, the biotin-avidin system can be used for binding an antibody or an antigen with a labeling agent.

Upon insolubilization of an antigen or an antibody, physical adsorption may be used, or chemical bonding normally used for insolubilizing or immobilizing a protein or an enzyme may be used. As the carrier, for example, insoluble polysaccharides such as agarose, dextran and cellulose, synthetic resins such as polystyrene, polyacrylamide and silicone, and glass are used.

In a sandwich method, the present protein in a specimen solution can be quantitated by reacting a specimen solution with the present monoclonal antibody (primary reaction), further reacting with another present monoclonal antibody labeled, (secondary reaction) and measuring the activity of a labeling agent on an insolubilized carrier. The primary reaction and the secondary reaction may be performed in a reverse order, or, alternatively, they may be performed simultaneously or at different times. The labeling agent and the insolubilizing method can be according to those described above. In addition, in an immunoassay by a sandwich method, an antibody used for a solid phase antibody or a labeling antibody is not necessarily one kind, and a mixture of 2 or more kinds of antibodies may be used for the purpose of enhancing the measuring sensitivity.

In a method for measuring the present protein by the present sandwich method, as the present monoclonal antibodies used for the primary reaction and the secondary reaction, antibodies having a different site to which the present protein is binded are preferably used. That is, in antibodies used for the primary reaction and the secondary reaction, for example, when an antibody used for secondary reaction recognizes a C-terminal of the present protein, as an antibody used for the primary reaction, an antibody which preferably recognizes a part other than a C-terminal part, for example, a N-terminal part is used.

The present monoclonal antibody can be used for a measuring system other than the sandwich method, for example, a competitive method, an immunometric method or nephrometry. In the competitive method, after an antigen in a specimen solution and a labeled antigen are reacted with an antibody competitively, an unreacted labeled antigen (F) and a labeled antigen bound to an antibody (B) are separated (B/F separation), a labeled amount of either of B or F is measured and an antigen in the specimen solution is quantitated. In the present reaction method, there are used a solution method in which a soluble antibody is used as an antibody and polyethylene glycol and the second antibody to the above antibody are used for B/F separation, and a solid phased method in which a solid phased antibody is used as the first antibody, or a soluble antibody is used as the first antibody and a solid phased antibody is used as the second antibody.

In the immunometric method, an antigen in a specimen solution and a solid phased antigen are reacted competitively with a predetermined amount of a labeled antibody, then a solid phase and a solution phase are separated, or an antigen in a specimen solution and an excessive amount of a labeled antibody are reacted, then a solid phased antigen is added to bind an unreacted labeled antibody to a solid phase, and a solid phase and a solution phase are separated. Then, a labeled amount of either phase is measured to quantitate an antigen in a specimen solution.

In addition, in nephrometry, an amount of insoluble precipitates produced as a result of an antigen-antibody reaction in a gel or a solution is measured. Even when an amount of an antigen in a specimen solution is small and only a small of amount of precipitates are obtained, laser nephrometry utilizing laser scattering is suitably used.

When these individual immunoassays are applied to the present measuring method, setting of the special conditions and operations is not required. The system for measuring the present protein may be constructed by adding the normal technical consideration of a person skilled in the art to the normal conditions and operations in respective methods. For the details of these general technical means, review and books may be referenced [for example, see "Radioimmunoassay" ed. by Hiroshi Irie (published by Kodansha in 1974), "Radioimmunoassay, Second Series" ed. by Hiroshi Irie (published by Kodansha in 1979), "Enzyme Immunoassay" ed. by Eiji Ishikawa et al. (published by Igakushoin in 1978), "Enzyme Immunoassay" ed. by Eiji Ishikawa et al. (2nd edition) (published by Igakushoin in 1982), "Enzyme Immunoassay" ed. by Eiji Ishikawa et al. (3rd edition) (published by Igakushoin in 1987), "Methods in ENZYMOLOGY" vol. 70 (Immunochemical Techniques (Part A)), ibid. Vol. 73 (Immunochemical Techniques (Part B), ibid. Vol. 74 (Immunochemical Techniques (Part C), ibid. Vol. 84 (Immunochemical Techniques (Part D: Selected Immunoassays )), ibid. Vol. 92 (Immunochemical Techniques (Part E:Monoclonal Antibodies and General Immunoassay Methods)), ibid. Vol. 121 (Immunochemical Techniques (Part 1:Hybridoma Technology and Monoclonal Antibodies)) all published by Acadeic Press Inc.].

As described above, by using the present antibody, the present protein can be quantitated with the better sensitivity.

Further, when overexpression of the present protein can be detected by quantitating the present protein in the living body using the present antibody, it can be diagnosed that there is a high possibility that there are or there will be in the future cardiac infarction and dysfunction accompanying therewith, unstable angina, restenosis after PTCA, arrhythmia, heart failure, hypertension and tissue disorder accompanying therewith, cerebral infarction, cerebral hemorrhage, subarachnoid hemorrhage and cerebral disorder accompanying therewith. That is, the present antibody is useful as a drug for diagnosing the above diseases.

(3) Neutralizing Antibody

Among the present antibodies, a neutralizing antibody which can bind to an extracellular region of the present protein and inhibit the functions (for example, $Na^+$—$HCO_3^-$ cotransporter activity) of the present protein can be used as a composition for treating and/or preventing for ischemic diseases (for example, cardiac infarction and dysfunction accompanying therewith, unstable angina and the like), restenosis after PTCA, arrhythmia, heart failure, hypertension and tissue disorder accompanying therewith, and ischemic brain diseases (for example, brain disorder accompanying with cerebral infarction, cerebral hemorrhage and subarachnoid hemorrhage and the like). The present antibody can be formulated into preparations, as it is, or together with a physiologically acceptable carrier such as supplementary drug for uptake promotion, and can be administered to a human being or a warm-blooded animal.

(4) Antisense DNA

An antisense DNA which can complementarily bind to the present DNA and inhibit expression of the DNA can inhibit the functions of the present protein or DNA in the living body, it can be used as a composition for treating and/or preventing for ischemic diseases (for example, cardiac infarction and dysfunction accompanying therewith, unstable angina and the like), restenosis after PTCA, arrhythmia, heart failure, hypertension and tissue disorder accompanying therewith, and ischemic brain diseases (for example, brain disorder accompanying with cerebral infarction, cerebral hemorrhage and subarachnoid hemorrhage and the like).

When the above antisense DNA is used as the above composition for treatment and/or prevention, the present antisense DNA can be administered to a human being or a warm-blooded animal according to the intentional means, as it is, or after inserted into a suitable vector such as retrovirus vector, adenovirus vector, and adenovirus-associated virus vector. The present antisense DNA can be formulated into preparations, as it is, or together with a physiologically acceptable carrier such as a complementary drug for uptake promotion, and can be administered by a gene gun or a catheter such as a hydrogel catheter.

As the antisense DNA having a nucleotide sequence substantially complementary to that of present DNA, any antisense DNAs may be used as long as they have a nucleotide sequence substantially complementary to that of the present DNA and have the action which can inhibit expression of the DNA.

An example of the nucleotide sequence substantially complementary to that of the present DNA includes a nucleotide sequence having about 80% or more, preferably about 90% or more, more preferably about 95% or more, further preferably about 98% or more, most preferably about 99% or more homology with a whole nucleotide sequence or a partial nucleotide sequence of a nucleotide sequence complementary to that of present DNA (that is, a complementary strand for the present DNA). In particular, among a whole nucleotide sequence of a complementary strand for the present DNA, an antisense DNA having about 80% or more, preferably about 90% or more, more preferably about 95% or more, further preferably about 98% or more, most preferably about 99% or more homology with a complementary strand for a nucleotide sequence of a part encoding a N-terminal site of the present protein or a partial peptide thereof (for example, a nucleotide sequence near an initiation codon) is suitable. These antisense DNAs can be prepared using the known DNA synthesizer.

(5) Preparation of Non-human Animal Having DNA Encoding Present Protein

A transgenic non-human animal expressing the present protein can be prepared using the present DNA. Examples of the non-human animal include a mammal (for example, rat, mouse, rabbit, sheep, pig, cow, cat, dog and monkey) (hereinafter, abbreviated as animal). In particular, mouse and rat are preferable.

Upon transference of the present DNA into a subject animal, it is generally advantageous to use the DNA as a gene construct binded to understream of a promoter which can express in an animal cell. For example, when the present DNA derived from a rat is transferred, a gene construct which is binded to understream of various animal-derived promoters having the high homology therewith and which can express the present DNA in an animal cell can be micro-injected into a rat fertilized egg to make a DNA transferred animal which can produce highly the present protein. As this promoter, for example, ubiquitous expression promoters such as virus-derived promoters, metallothionein promoter and the like can be used. Preferably, gene promoters which are specifically expressed in heart are used.

Transference of the present DNA at a fertilized egg cell stage is assured so that the DNA is present in all of germ cells and somatic cells in a subject animal. Existence of the present protein in a germ cell of a produced animal after DNA transference means that all progeny of the produced animal all have the present protein in all of germ cells and somatic cells. The progeny of this kind of animal which inherited the gene has the present protein in all of the germ cells and somatic cells.

The present DNA transferred animal can be reared and passaged as the DNA harboring animal under the normal rearing environment by assuring that a gene is stably held by mating. Further, breeding and passage can be performed so that all the progeny has the DNA by making female and male animals harboring the desired DNA to obtain a homozygote animal having an introduced gene in both homologous chromosomes, and mating these female and male animals.

Since an animal with present DNA transferred is made to highly express the present protein, it is useful as an animal for screening a drug acting on the present protein.

The present DNA transferred animal can be used also as a cell source for tissue culturing. For example, the present protein can be analyzed by directly analyzing a DNA or a RNA in tissues of the present DNA transferred rat, or analyzing tissues in which the present protein expressed by the gene is present. Cells of the tissues harboring the present protein can be cultured by standard tissue culturing tequniques and they can be used to study the functions of cells from the tissues which are generally difficult to culture, like cells derived from brain or peripheral tissues. In addition, by using the cell, for example, it is possible to select a drug which enhances the functions of various tissues. In addition, when there is a high expressing cell strain, the present protein can be isolated and purified therefrom.

In the present specification and drawings, when a base and an amino acid are expressed by abbreviation, it is based on abbreviation by IUPAC-IUB Commission on Biochemical Nomenclature or the conventional abbreviation in the art, examples of which are described below. In addition, when an optical isomer may be present regarding an amino acid, a L isomer is shown unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| R | ribonucleic acid |
| mRNA | messenger ribonucleic acid |
| dATP | deoxyadenosine triphosphate |
| dTTP | deoxythymidine triphosphate |
| dGTP | deoxyguanosin triphosphate |
| dCTP | deoxycytidine triphosphate |
| ATP | adenosine triphosphate |
| EDTA | ethylenediamine tetraacetate |
| SDS | sodium dodecylsulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGLU | pyroglutamic acid |
| Me | methyl group |
| Et | ethyl group |
| Bu | butyl group |
| Ph | phenyl group |
| TC | thiazolydine-4 (R)-carboxamido group |

In addition, substituents, protecting groups and reagents which are frequently used in the present specification are expressed by the following symbols:

| | |
|---|---|
| Tos | T-toluene sulfonyl |
| CHO | formyl |
| Bzl | benzyl |
| Cl$_2$Bzl | 2,6-dichlorobenzyl |
| Bom | benzyloxymethyl |
| Z | benzyloxycarbonyl |

-continued

| Cl-Z | 2-chlorobenzyloxycarbonyl |
| Br-Z | 2-bromobenzyloxycarbonyl |
| Boc | t-butoxycarbonyl |
| DNP | dinitrophenyl |
| Trt | trityl |
| Bum | t-butoxymethyl |
| Fmoc | N-9-fluorenylmethoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dicyclohexylcarbodiimide |

Sequence numbers of Sequence Listings in the present specification indicate the following sequences:

[SEQ ID NO.: 1]
Indicates an amino acid sequence of the present protein.

[SEQ ID NO.: 2]
Indicates a nucleotide sequence of a DNA encoding of the present protein having an amino acid sequence represented by SEQ ID NO.: 1.

[SEQ ID NO.: 3]
Indicates a nucleotide sequence of a primer used for cloning a DNA encoding the present human heart-derived protein.

[SEQ ID NO.: 4]
Indicates a nucleotide sequence of a primer used for cloning a DNA encoding the present human heart-derived protein.

[SEQ ID NO.: 5]
Indicates a nucleotide sequence of a primer used for cloning a DNA encoding the present human heart-derived protein.

[SEQ ID NO.: 6]
Indicates a nucleotide sequence of a primer used for cloning a DNA encoding the present human heart-derived protein.

[SEQ ID NO.: 7]
Indicates a nucleotide sequence of a DNA fragment of the present human heart-derived protein used for Northern blotting of Example 2.

[SEQ ID NO.: 8]
Indicates a nucleotide sequence of a DNA fragment of a human retina-derived $Na^+$—$HCO_3^-$ cotransporter used for Northern blotting of Example 2.

A transformant Escherichia coli JM109/pMSR αNBC26 NEO obtained in Example 1 described below has been deposited to National Institute of Bioscienc and Human Technology of Agency of Industrial Science and Technology of the Ministry of International Trade and Industry (NIBH) on Nov. 24, 1998 under the deposition No. FERM BP-6585 and to Institute for Fermentation, Osaka (IFO) on Nov. 5, 1998 under the deposition number IFO 16215.

EXAMPLES

The present invention is described in the details in the following examples, which are not intended to restrict the invention. The gene manipulations using Escherichia coli were according to a method described in Molecular Cloning.

EXAMPLE 1

Cloning of and Determination of a Nucleotide Sequence of cDNA Encoding Human Heart-derived Protein Cloning of the former part of a cDNA encoding a human heart-derived protein was performed using a gene trapper positive selection system (manufactured by Life Technology).

The human heart-derived plasmid cDNA library (manufactured by Life Technology) was digested with Gene II and ExoIII to prepare a single-stranded cDNA library. On the other hand, a synthetic oligonucleotide (SEQ ID NO.: 3) was used as a probe for screening a cDNA library. The probe was labeled by biotinating a 3'-terminal using TdT, biotin-14-dCTP. The single-stranded cDNA library was treated at 95° C. for 1 minute, cooled rapidly in an ice, and a biotinated probe was added to perform hybridization at 37° C. for 1 hour. After hybridization, magnet beads were added, which were allowed to stand for 30 minutes while stirring at room temperature every 2 minutes. Thereafter, the mixture was placed in a magnetic rack and allowed to stand for 2 minutes. The supernatant was discarded, and magnet beads were washed with a wash buffer three times. After placed in a magnetic rack to allowed to stand, the supernatant was discarded, and an eluting buffer was added to allow to stand at room temperature for 5 minutes. After placed in a magnetic rack to allow to stand for 5 minutes, the DNA solution in the supernatant was recovered.

An synthetic oligonucleotide (SEQ ID NO.: 3) was added to the obtained DNA solution as a primer, which was allowed to stand at 95° C. for 1 minute. A repair enzyme was added to allow to stand at 70° C. for 15 minutes, and a double-stranded DNA was introduced into Escherichia coli DH10 B strain by an electroporation apparatus (manufactured by Bio Rad) The resulting transformant was used to perform screening by colony PCR using 2 oligonucleotides (SEQ ID NO.: 3 and SEQ ID NO.: 4) as a primer. Colonies in which a 0.24 (Kbp) amplified fragment was formed by PCR were selected as a positive clone.

After selected Escherichia coli was cultured, a plasmid was extracted, a nucleotide sequence of a cDNA was determined using a 377 DNA sequencer (manufactured by Perkin Elmer).

Cloning of the latter part of a cDNA encoding a human heart-derived protein was performed by PCR using a human heart-derived plasmid cDNA library (manufactured by Life Technology) as a template. PCR was carried out using synthetic nucleotides (SEQ ID NO.: 5 and SEQ ID NO.: 6) as a primer. A PCR reaction was performed by the Hot Start Method using Ampliwax PCR Gem 100 (manufactured by TAKARASHUZOU). As a lower layer mixed solution, 2 μl of 10×LA taq Buffer (manufactured by TAKARASHUZOU), 4 μl of a 2.5 mM dNTP solution, each 1 μl of a 10 μM primer solution, and 12 μl of a sterile distilled water were mixed. As an upper layer mixed solution, 0.7 μl of a human brain and heart-derived cDNA library solution, 3 μl of a 10×LA taq Buffer (manufactured by TAKARASHUZOU), 4 μl of a 2.5 mM dNTP solution, 5 μl of 20 mM magnesium chloride, 0.5 μl of a LA taq DNA polymerase (manufactured by TAKARASHUZOU) and 16.8 μl of sterile distilled water were mixed. One Ampliwax PCR Gem 100 was added to the prepared lower layer mixed solution, treated at 94° C. for 1 minute and at 4° C. for 5 minutes, and the upper layer mixed solution was added to prepare a reaction solution for PCR. Under the reaction conditions, after 1 cycle at 94° C. for 30 seconds, a cycle at 94° C. for 30 seconds and at 68° C. for 4 minutes was repeated 45 times. When the reaction solution was subjected to electrophoresis on 1% agarose gel, a DNA fragment (about 0.6 kd) considered to encode a 3' region was specifically amplified. The DNA fragment was recovered from the agarose gel according to the conventional method and subcloned into pT7 Blue (manufactured by Promega) by a DNA Ligation kit (manufactured by TAKARASHUZOU).

A plasmid having a cDNA encoding the former part was digested with restriction enzymes Hind III (manufactured by TAKARASHUZOU) and EcoRI (manufactured by TAKARASHUZOU), and subjected to electrophoresis on 1% agarose gel, and a 0.6 kb DNA fragment was recovered. In addition, a plasmid having a cDNA encoding the latter part was digested with restriction enzymes SalI (manufactured by TAKARASHUZOU) and EcoRI (manufactured by TAKARASHUZOU), and subjected to electrophoresis on 1% agarose gel, and a 2.6 kb DNA fragment was recovered.

The plasmid pBluescript II SK+was cut with Sal I (manufactured by TAKARASHUZOU) and Hind III (manufactured by TAKARASHUZOU) to obtain a 3.0 kb DNA fragment. The above 3.0 kb DNA fragment, the 2.6 kb DNA fragment encoding the former part of the previously prepared human heart-derived protein, and the 0.6 kb DNA fragment encoding the latter part were mixtured, ligated with a DNA Ligation kit (manufactured by TAKARASHUZOU), a competent cell of Escherichia coli JM109 (manufactured by TAKARASHUZOU) was transformed to prepare a plasmid pNBC2b. A nucleotide sequence of a cDNA was determined by a 377 DNA sequencer (manufacture by Perkin Elmer). The resulting cDNA had a nucleotide sequence represented by SEQ ID NO.: 2. This cDNA fragment encoded a novel protein comprising 971 amino acids represented by SEQ ID NO.: 1.

EXAMPLE 2

Confirmation of Expression Specificity in Each Tissue (Northern Hybridization)

Specific analysis of a tissue in which a gene was expressed by Northern hybridization was performed using a membrane filter for Human Multiple Tissue Northern Blot (manufactured by Clonetech). This membrane filter was pre-hybridized at 50° C. for 3 hours in a pre-hybridization buffer (50% deionized formamide, 5×SSPE, 2×Denhart's solution, 2% SDS, 100 µg/ml heat denatured salmon sperm DNA). On the other hand, a DNA fragment specific for a gene encoding the present protein represented by SEQ ID NO.: 7 as a probe was labeled with [α-$^{32}$P]dCTP (manufactured by Amersham) and Bca BEST labeling kit (manufactured by TAKARASHUZOU). Hybridization was performed at 64° C. for 1 hour in an express hybridization buffer containing a labeling probe.

Figure 5:
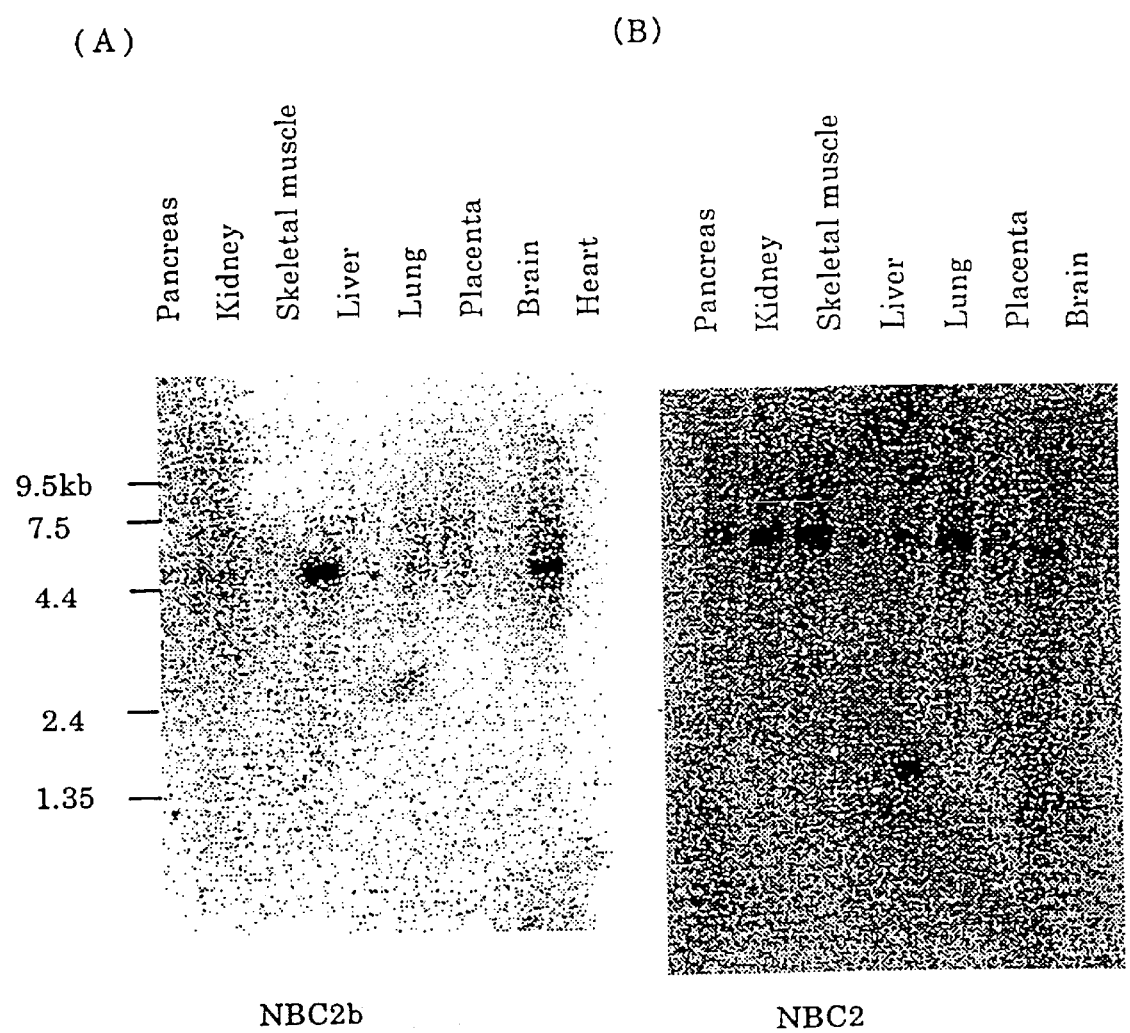
FIG. 5 shows the results of an amount of expression of a mRNA encoding the present heart-derived protein in each tissue of a human being, which was examined by Northern hybridization.

The filter was washed two times in a 2×SSC, 0.05% SDS solution at room temperature, and washed two times in a 0.1×SSC, 0.1% SDS solution at 50° C. An autoradiograph of a filter was taken with BAS 2000 (manufactured by Fuji film) and a band hybridized with a probe was detected. As a result, a band specific in heart and skeletal muscle was detected [FIG. 5-a].

On the other hand, by using a DNA fragment represented by SEQ ID NO.:8 as a probe specific for hNBC2 which is a human retina-derived protein, hybridization was performed under the similar conditions to those described above. As a result, a band of hNBC2 was detected in pancreas, kidney, skeletal muscle, lung, placenta and heart. [FIG. 5-b].

EXAMPLE 3

Construction of Expression Vector for a cDNA encoding Human Heart-derived Protein After the SRα promoter derived from pTB1411 described in JP-A 5-076385 was digested to blunt with BglII (manufactured by TAKARASHUZOU), the blunted digest was ligated to the pCI vector (manufactured by Promega) with a DNA Ligation kit (manufactured by TAKARASHUZOU) to obtain pCI-SRα. Then, this pCI-SRα was digested with Cla I (manufactured by Takarashuzou) and treated with T4 DNA polymerase (manufactured by Takarashuzou) to make ends blunt. On the other hand, after pGFP-C1 (manufactured by Toyobo) was digested with Bsu361 (manufactured by Daiichikagakuyakuhin), ends were blunted by treatment with a T4 DNA polymerase (manufactured by Takarashuzou), both were ligated with a DNA Ligation kit (manufactured by Takarashuzou), and a competent cell of Escherichia coli JM109 (manufactured by Takarashuzou) was transformed to obtain a plasmid pMSRαneo.

The plasmid pMSRαneo was cut with NotI (manufactured by TAKARASHUZOU) and SalI (manufactured by TAKARASHUZOU) to obtain a 5.4 kb DNA fragment. The plasmid pNBC2b was cut with NotI (manufactured by TAKARASHUZOU), SalI (manufactured by TAKARASHUZOU) and XmnI (manufactured by New England Biolab) to obtain a 3.3 kb DNA fragment. The previously prepared 5.4 kb DNA fragment and the 3.2 kb DNA fragment were mixed, ligated with a DNA Ligation kit (manufactured by Takarashuzou), and a competent cell of Escherichia coli JM109 (manufactured by Takarashuzou) was transformed to prepare a plasmid pMSRαNBC26neo. The plasmid pMSRαNBC26neo harboring a DNA encoding the present heart-derived protein was introduced into Escherichia coli JM109 to obtain a transformant: Escherichia coli JM109/pMSRαNBC26neo.

EXAMPLE 4

Introduction of a Plasmid for Expressing Human Heart-derived Protein Into CHO-K1 Cell and Obtaining of Expressing Cell CHO-K1 cell which had grown in a 150 ml tissue culture flask (Corning) using Ham F12 medium (manufactured by Nissuiseiyaku) containing 10% bovine fetal serum (manufactured by Life Technologies, Inc., USA) was peeled with 0.5 g/L trypsin-0.2 g/L EDTA (manufactured by Life Technologies, Inc., USA), the cells were washed with PBS (manufactured by Life Technologies, Inc., USA), centrifuged (1000 rpm, 5 minutes) and suspended with PBS. Then, a DNA was introduced into a cell using a gene pulser (manufactured by BioRad) according to the following conditions. That is, 8×10$^6$ cells and 10 µg of the plasmid pMSRαNBC26neo for expressing human heart-derived novel protein were added to a cuvette with 0.4 cm gap, and electroporation was performed under voltage 0.25 kV and capacitance 960 µF. Thereafter, cells were transferred to Ham F12 medium containing 10% bovine fetal serum, cultured for 24 hours, cells were peeled again and centrifuged and, then, suspended in Ham F12 medium containing 10% bovine fetal serum to which geneticin (manufactured by Life Technologies, Inc.; USA) had been added to 500 µg/ml, diluted to 10$^4$ cells/ml, which were seeded on a 96-well plate (manufactured by Corning Costar Corporation, USA) and cultured in a carbonic gas incubator at 37° C. to obtain a Genetecin-resistant transformant.

Then, the resulting transformant was seeded on a 96-well white plate and cultured in a carbonic gas incubator at 37° C. for 48 hours. After washed with 150 µl of A solution (140 mM tetramethylammonium chloride, 25 mM potassium bicarbonate, 0.8 mM dipotassium phosphate, 0.2 mM monopotassium phosphate, 1 mM calcium chloride, 1 mM magnesium chloride, 10 mM HEPS, pH 7.4), 150 µl of B solution (100 mM tetramethylammonium chloride, potassium bicarbonate, 0.8 mM dipotassium phosphate, 0.2 mM monopotassium phosphate, 1 mM calcium chloride, 1 mM magnesium chloride, 40 mM ammonium chloride, 10 mM HEPES, pH7.4) containing 5 μM BCECF-AM (manufactured by Dojinsha) were added to cells, which were incubated at room temperature for 15 minutes. The solution was aspiration-removed, washed with 150 μl of A solution, the solution was aspiration-removed, 50 μl of A solution containing 1 mM amymoride (manufactured by Sigma) was added, and variation in an intracellular pH was measured with a fluorescent drug screening system FDSS 2000 (manufactured by Hamamatsu Photonics). 200 μl of C solution (115 mM sodium chloride, 25 mM potassium chloride, 25 mM sodium bicarbonate, 0.8 mM dipotassium phosphate, 0.2 mM monopotassium phosphate, 1 mM calcium chloride, 1 mM magnesium chloride, 1 mM amyloride (manufactured by Sigma), 10 mM HEPES, pH 4) was added and, thereafter, a strain, hNBC2b-33/CHO-K1 cell in which an increase in an intracellular pH had been recognized was selected.

EXAMPLE 5

Analysis of Functions of Human Heart-derived Protein by Intracellular pH Measurement hNBC2b-33/CHO-K1 cell which had been cultured in Ham F12 medium (manufactured by Nissuiseiyaku) containing 10% bovine fetal serum (manufactured by Life Technologies, Inc.; USA) and wild type CHO-K1 cell as a control were seeded on a 96-well white plate to $2 \times 10^4$ cells/well, and cultured in a carbonic gas incubator at 37° C. for 48 hours. After 150 μl of A solution (140 mM tetramethylammonium chloride, 25 mM potassium bicarbonate, 0.8 mM dipotassium phosphate, 0.2 mM monopotassium phosphate, 1 mM potassium chloride, 1 mM magnesium chloride, 10 mM HEPES, pH7.4), and 150 μl of B solution (100 mM tetramethylammonium chloride, potassium bicarbonate, 0.8 mM dipotassium phosphate, 0.2 mM monopotassium phosphate, 1 mM calcium chloride, 1 mM magnesium chloride, 40 mM ammonium chloride, 10 mM HEPES, pH7.4) containing 0.5 μM BCECF-AM (manufactured by Dojinsha) was added to cells, which was incubated at room temperature for 15 minutes. The solution was aspiration-removed, washed with 150 μl of A solution, the solution was aspiration-removed, 150 μl of A solution containing 1 mM amyloride (manufactured by Sigma) was added, and variation in an intracellular pH was measured with a fluorescent drug screening system FDSS 2000 (Hamamatsu Photonics). 200 μl of C solution (115 mM sodium chloride, 25 mM potassium chloride, 25 mM sodium bicarbonate, 0.8 mM dipotassium phosphate, 0.2 mM monopotassium phosphate, 1 mM potassium chloride, 1 mM magnesium chloride, 1 mM amyloride (manufactured by Sigma), 10 mM HEPES, pH 7.4) was added, and an increased amount of an intracellular pH increased in 1 minute (a ratio of fluorescent values at 450 nm and 490 nm (450 nm/490 nm)) was calculated. Further, an increased amount of an intracellular pH to which an anion exchanger inhibitor DIDS (4,4'-diisothiocyanatostilbene-2,2'-disulfonic acid) (manufactured by Sigma) was added was measured. As a result, a significant increase in an intracellular pH (significance test by t test, $p<0.001$) was recognized as compared with wild-type CHO-K1 cell in hNBC2b-33/CHO-K1 cell in which the present human heart-derived protein was expressed, after C solution containing sodium ions and bicarbonate ions were added. Further, an increase in an intracellular pH was suppressed by the addition of DIDS which is an inhibitor for an anion transporter [FIG. 6].

The present protein and the present DNA can be used as or for [1] obtaining an antibody and antiserum, [2] constructing an expression system for the present protein, [3] development of a system for measuring the activity of a $Na^+$—$HCO_3^-$ cotransporter and screening of a drug candidate compound using the same expression system, [4] performing drug design based on the steric structure of a $Na^+$—$HCO_3^-$ cotransporter protein, [5] a reagent for making a probe or a PCR primer in gene diagnosis, [6] making a transgenic animal, or [7] a composition for gene prevention and/or treatment.

---

What is claimed is:

1. An isolated protein comprising an amino acid sequence represented by SEQ ID NO: 1, or a salt of said protein.

2. The protein or salt thereof according to claim 1, which has a Na$^+$—HCO$_3^-$ cotransporter activity.

3. An isolated protein comprising an amino acid sequence which has 90% homology with an amino acid sequence represented by SEQ ID NO: 1, or a salt of said protein, said protein or salt thereof having a Na$^+$—HCO$_3^-$ cotransporter activity.

4. A kit comprising the protein or salt thereof according to claim 1.

5. A kit comprising the protein or salt thereof according to claim 2.

6. A kit comprising the protein or salt thereof according to claim 3.

7. A method for identifying a compound, or a salt of the compound, which promotes or inhibits $Na^+$—$HCO_3^-$ cotransporter activity of the protein or salt thereof according to claim 1, said method comprising (a) measuring the $Na^+$—$HCO_3^-$ cotransporter activity of the protein or salt thereof, (b) contacting the protein or salt thereof, with the compound or salt of the compound, (c) measuring the $Na^+$—$HCO_3^-$ cotransporter activity of the contacted protein or salt thereof, (d) comparing the $Na^+$—$HCO_3^-$ cotransporter activity obtained in step (c) with the $Na^+$—$HCO_3^-$ cotransporter activity obtained in step (a) to identify a compound or salt thereof which promotes or inhibits the $Na^+$—$HCO_3^-$ cotransporter activity of the protein or salt thereof according to claim 1.

8. A method for identifying a compound, or a salt of the compound, which promotes or inhibits $Na^+$—$HCO_3^-$ cotransporter activity of the protein or salt thereof according to claim 3, said method comprising (a) measuring the $Na^+$—$HCO_3^-$ cotransporter activity of the protein or salt thereof, (b) contacting the protein or salt thereof, with the compound or salt of the compound, (c) measuring the $Na^+$—$HCO_3^-$ cotransporter activity of the contacted protein or salt thereof, (d) comparing the $Na^+$—$HCO_3^-$ cotransporter activity obtained in step (c) with the $Na^+$—$HCO_3^-$ cotransporter activity obtained in step (a) to identify a compound or salt thereof which promotes or inhibits the $Na^+$—$HCO_3^-$ cotransporter activity of the protein or salt thereof according to claim 3.

\* \* \* \* \*